United States Patent
Freeman

(10) Patent No.: US 9,987,193 B2
(45) Date of Patent: Jun. 5, 2018

(54) AUTOMATED RESUSCITATION DEVICE WITH VENTILATION SENSING AND PROMPTING

(71) Applicant: ZOLL Medical Corporation, Chelmsford, MA (US)

(72) Inventor: Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days. days.

(21) Appl. No.: 15/194,542

(22) Filed: Jun. 27, 2016

(65) Prior Publication Data

US 2016/0374894 A1 Dec. 29, 2016

Related U.S. Application Data

(63) Continuation of application No. 12/651,556, filed on Jan. 4, 2010, now Pat. No. 9,375,381, which is a (Continued)

(51) Int. Cl.
*A61N 1/00* (2006.01)
*A61H 31/00* (2006.01)
(Continued)

(52) U.S. Cl.
CPC ......... *A61H 31/005* (2013.01); *A61H 31/007* (2013.01); *A61M 16/021* (2017.08);
(Continued)

(58) Field of Classification Search
CPC .... A61H 31/00; A61H 31/004–31/007; A61M 16/0069; A61M 16/024;
(Continued)

(56) References Cited

U.S. PATENT DOCUMENTS 4,019,501 A   4/1977   Harris
4,077,400 A   3/1978   Harrigan
(Continued)

FOREIGN PATENT DOCUMENTS

EP   1491175   12/2004
EP   1157717   1/2005
(Continued)

OTHER PUBLICATIONS

"Guidelines 2000 for Cardiopulmonary Resuscitation and Emergency Cardiovascular Care. Supplement to Circulation," vol. 102, No. 8, Aug. 8, 2000, p. I-67.
(Continued)

*Primary Examiner* — Scott Getzow
(74) *Attorney, Agent, or Firm* — Fish & Richardson P.C.

(57) ABSTRACT

A device for assisting a caregiver in delivering cardiac resuscitation to a patient, the device comprising a user interface configured to deliver prompts to a caregiver to assist the caregiver in delivering cardiac resuscitation to a patient; at least one sensor configured to detect the caregiver's progress in delivering the cardiac resuscitation, wherein the sensor is configured to provide a signal containing information indicative of ventilation; a memory in which a plurality of different prompts are stored, including at least one ventilation progress prompt to guide the rescuer's performance of ventilation; a processor configured to process the output of the sensor to determine a parameter descriptive of ventilation progress and to determine whether the ventilation progress prompt should be selected for delivery. Possible parameters descriptive of ventilation progress include ventilation rate, delivered tidal volume, and flow rate.

10 Claims, 22 Drawing Sheets

Related U.S. Application Data continuation of application No. 11/384,218, filed on Mar. 17, 2006, now Pat. No. 7,747,319.

(51) Int. Cl.
*A61M 16/04* (2006.01)
*A61N 1/39* (2006.01)
*A61M 16/00* (2006.01)

(52) U.S. Cl.
CPC ........ *A61M 16/04* (2013.01); *A61M 16/0488* (2013.01); *A61N 1/39* (2013.01); *A61N 1/3925* (2013.01); *A61N 1/3937* (2013.01); *A61N 1/3993* (2013.01); *A61H 2031/002* (2013.01); *A61H 2201/5007* (2013.01); *A61H 2201/5043* (2013.01); *A61H 2201/5048* (2013.01); *A61H 2201/5071* (2013.01); *A61H 2201/5084* (2013.01); *A61H 2230/40* (2013.01); *A61M 16/0411* (2014.02); *A61M 2016/003* (2013.01); *A61M 2016/0015* (2013.01); *A61M 2016/0027* (2013.01); *A61M 2205/332* (2013.01); *A61M 2205/505* (2013.01); *A61M 2205/581* (2013.01); *A61M 2205/583* (2013.01); *A61M 2205/587* (2013.01); *A61M 2230/42* (2013.01)

(58) Field of Classification Search
CPC .. A61M 16/026; A61M 16/022; A61M 16/00; A61M 2016/0015
See application file for complete search history.

(56) References Cited

U.S. PATENT DOCUMENTS

| | | | |
|---|---|---|---|
| 4,095,590 A | 6/1978 | Harrigan | |
| 4,588,383 A | 5/1986 | Parker et al. | |
| 4,610,254 A | 9/1986 | Morgan et al. | |
| 4,863,385 A * | 9/1989 | Pierce | G09B 23/288 434/265 |
| 5,496,257 A | 3/1996 | Kelly | |
| 5,626,151 A | 5/1997 | Linden | |
| 5,662,690 A | 9/1997 | Cole et al. | |
| 5,700,281 A | 12/1997 | Brewer et al. | |
| 5,913,685 A | 6/1999 | Hutchins | |
| 6,125,299 A | 9/2000 | Groenke et al. | |
| 6,306,107 B1 | 10/2001 | Myklebust et al. | |
| 6,334,070 B1 | 12/2001 | Nova et al. | |
| 6,351,671 B1 | 2/2002 | Myklebust et al. | |
| 6,356,785 B1 | 3/2002 | Snyder et al. | |
| 6,390,996 B1 | 5/2002 | Halperin et al. | |
| 6,821,254 B2 | 11/2004 | Weil et al. | |
| 6,827,695 B2 | 12/2004 | Palazzolo et al. | |
| 7,647,723 B2 | 1/2010 | Klein et al. | |
| 7,747,319 B2 | 6/2010 | Freeman | |
| 9,375,381 B2 | 6/2016 | Freeman | |
| 2002/0188332 A1 | 12/2002 | Lurie et al. | |
| 2003/0233129 A1 | 12/2003 | Matos | |
| 2004/0162587 A1 | 8/2004 | Hampton et al. | |
| 2004/0176807 A1 | 9/2004 | Freeman | |
| 2004/0267325 A1 | 12/2004 | Geheb et al. | |
| 2005/0085799 A1 | 4/2005 | Luria et al. | |
| 2005/0267536 A1 | 12/2005 | Freeman et al. | |
| 2006/0005835 A1 | 1/2006 | Berthon-Jones | |
| 2006/0015044 A1 * | 1/2006 | Stavland | A61B 5/0535 601/41 |
| 2006/0027234 A1 * | 2/2006 | Gradon | A61M 16/10 128/204.21 |
| 2006/0229680 A1 | 10/2006 | Chapman et al. | |
| 2009/0036790 A1 * | 2/2009 | Landesberg | A61B 5/08 600/529 |

FOREIGN PATENT DOCUMENTS

| | | |
|---|---|---|
| JP | 63-90204 | 7/1988 |
| WO | 99/24114 | 5/1999 |
| WO | 00/66215 | 11/2000 |
| WO | 00/69338 | 11/2000 |
| WO | 01/22885 | 4/2001 |
| WO | 01/56652 | 8/2001 |
| WO | 01/66182 | 9/2001 |
| WO | 04/058351 | 7/2004 |

OTHER PUBLICATIONS

"Guidelines 2000 for Cardiopulmonary Resuscitation and Emergency Cardiovascular Care. Supplement to Circulation," vol. 102, No. 8, Aug. 8, 2000, p. I-32, Figs. 7 and 8.

U.S. Appl. No. 09/962,834, filed Sep. 14, 2001.

European Search Report issued in European Application No. 15167571.7 dated Sep. 1, 2017.

* cited by examiner

| PROMPT # | PROMPT |
|---|---|
| 1 | CHECK RESPONSIVENESS, SHOUT ARE YOU OK, |
| 2 | IF UNRESPONSIVE, SHOUT HELP LOUDLY |
| 3 | CALLING 911 |
| 4 | FOLLOW LIT PICTURES |
| 5 | LOOK CAREFULLY AT THE PICTURE SHOWN ON THE COVER. |
| 6 | PLACE PERSON ON THEIR BACK WITH THE COVER UNDERNEATH THE SHOULDERS AS SHOWN IN THE PICTURE. |
| 7 | THE COVER IS UPSIDE DOWN. PLEASE PLACE THE COVER WITH THE INSTRUCTION LABEL FACING YOU. |
| 8 | PLACE THE VICTIM'S SHOULDERS DIRECTLY ON THE COVER AS SHOWN ON THE INSTRUCTION LABEL. |
| 9 | TILT HEAD AND LIFT CHIN AS SHOWN IN THE LIT PICTURE TO OPEN THE PERSON'S AIRWAY. |
| 10 | KNEEL BESIDE THE PERSON'S RIGHT SHOULDER. CHECK BREATHING BY PLACING YOUR EAR OVER THE VICTIM'S NOSE AND MOUTH WHILE MAINTAINING AN OPEN AIRWAY. |
| 11 | LOOK FOR THE CHEST TO RISE AND FALL, LISTEN FOR AIR ESCAPING WHILE BREATHING, AND FEEL FOR THE FLOW OF AIR. |
| 12 | IF NOT BREATHING THEN TILT HEAD, LIFT CHIN, AND PINCH NOSE AS SHOWN IN LIT PICTURE AND GIVE VICTIM TWO BREATHS |
| 13 | MAKE SURE TO BREATHE MORE DEEPLY INTO PATIENT. |
| 14 | CHECK PULSE. PLACE FINGERS AS SHOWN IN LIT PICTURE AT THE SIDE OF THE NECK. |
| 15 | PRESS GENTLY TO FEEL FOR PULSE. |
| 16 | IF NO DETECTED PULSE, THE PERSON IS PROBABLY IN CARDIAC ARREST. |
| 17 | REMOVE CLOTHING FROM VICTIM'S CHEST |
| 18 | OPEN WHITE ELECTRODE PACKAGE |
| 19 | LOOK CAREFULLY AT PICTURE ABOVE RED CROSS |
| 20 | LOOK CAREFULLY AT PICTURE BESIDE RED ARROW TAB # 2 |
| 21 | PLACE RIGHT HAND ON RED CROSS |

FIG. 7A

| PROMPT # | PROMPT |
|---|---|
| 22 | PULL RED ARROW TAB # 2 (TO REMOVE WHITE PLASTIC) AS SHOWN IN PICTURE |
| 23 | THE BLUE BACKING STILL SEEMS TO BE ATTACHED TO THE WHITE PAD. YOU NEED TO REMOVE IT BEFORE YOU ATTACH THE ELECTRODES TO THE PATIENT. |
| 24 | PLEASE MAKE SURE THAT THERE ISN'T ANY CLOTHING UNDERNEATH THE WHITE FOAM PADS YOU PLACED ON THE VICTIM'S CHEST. |
| 25 | PRESS PAD FIRMLY TO VICTIM'S BARE CHEST |
| 26 | LOOK CAREFULLY AT PICTURE BESIDE RED ARROW TAB # 3 |
| 27 | PLACE LEFT HAND ON RED CROSS |
| 28 | PULL RED ARROW TAB # 3 (TO REMOVE WHITE PLASTIC) AS SHOWN IN PICTURE |
| 29 | GRAB RED PULL TAB ON THE CORNER OF THE WHITE PACKAGE AND PULL FIRMLY TO TEAR OPEN PACKAGE. IF UNABLE TO TEAR OPEN, CUT ALONG DOTTED LINE WITH SCISSORS. |
| 30 | PRESS PAD FIRMLY TO VICTIM'S BARE CHEST |
| 31 | PRESS FLASHING HEART |
| 32 | IF NO CIRCULATION PLACE HANDS ON RED CROSS AS INDICATED BY LIT PICTURE |
| 33 | PRESS DOWN HARD 15 TIMES THEN GIVE TWO BREATHS |
| 34 | PUSH FASTER |
| 35 | PUSH HARDER |

FIG. 7B

AUTOMATED RESUSCITATION DEVICE WITH VENTILATION SENSING AND PROMPTING

CROSS-REFERENCE TO RELATED APPLICATIONS

This application is a continuation application of and claims priority to U.S. application Ser. No. 12/651,556, filed on Jan. 4, 2010, which application is a continuation application of and claims priority to U.S. application Ser. No. 11/384,218, filed on Mar. 17, 2006, issued U.S. Pat. No. 7,747,319. Both applications are hereby incorporated by reference.

TECHNICAL FIELD

This invention relates to devices for assisting caregivers in delivering cardiac resuscitation therapy to a patient (e.g., automatic external defibrillators).

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy. The term basic life support (BLS) involves all the following elements: initial assessment; airway maintenance; expired air ventilation (rescue breathing); and chest compression. When all these elements are combined, the term cardiopulmonary resuscitation (CPR) is used.

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation, and other pulseless electrical activity. Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

After using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardiopulmonary resuscitation (CPR). CPR generally involves a repeating pattern of five or fifteen chest compressions followed by a pause during which two rescue breaths are given.

Defibrillation can be performed using an AED. The American Heart Association, European Resuscitation Council, and other similar agencies provide protocols for the treatment of victims of cardiac arrest that include the use of AEDs. These protocols define a sequence of steps to be followed in accessing the victim's condition and determining the appropriate treatments to be delivered during resuscitation. Caregivers who may be required to use an AED are trained to follow these protocols.

Most automatic external defibrillators are actually semi-automatic external defibrillators (SAEDs), which require the caregiver to press a start or analyze button, after which the defibrillator analyzes the patient's ECG rhythm and advises the caregiver to provide a shock to the patient if the electrical rhythm is shockable. The caregiver is then responsible for pressing a control button to deliver the shock. Following shock delivery, the SAED may reanalyze the patient's ECG rhythm, automatically or manually, and advise additional shocks or instruct the caregiver to check the patient for signs of circulation (indicating that the defibrillation treatment was successful or that the rhythm is non-shockable) and to begin CPR if circulation has not been restored by the defibrillation attempts. Fully automatic external defibrillators, on the other hand, do not wait for user intervention before applying defibrillation shocks. As used below, automatic external defibrillators (AED) include semi-automatic external defibrillators (SAED).

Both types of defibrillators typically provide an auditory "stand clear" warning before beginning ECG analysis and/or the application of each shock. The caregiver is then expected to stand clear of the patient (i.e., stop any physical contact with the patient) and may be required to press a button to deliver the shock. The controls for automatic external defibrillators are typically located on a resuscitation device housing.

AEDs are typically used by trained medical or paramedic caregivers, such as physicians, nurses, emergency medical technicians, fire department personnel, and police officers. The ready availability of on-site AEDs and caregivers trained to operate them is important because a patient's chances of survival from cardiac arrest decrease by approximately 10% for each minute of delay between occurrence of the arrest and the delivery of defibrillation therapy.

Trained lay caregivers are a new group of AED operators. For example, spouses of heart attack victims may become trained as lay caregivers. Lay caregivers rarely have opportunities to defibrillate or deliver CPR, and thus they can be easily intimidated by an AED during a medical emergency. Consequently, such lay providers may be reluctant to purchase or use AEDs when needed, or might tend to wait for an ambulance to arrive rather than use an available AED, out of concern that the lay provider might do something wrong.

Some trained medical providers, e.g., specialists such as obstetricians, dermatologists, and family care practitioners, also rarely have the opportunity to perform CPR and/or defibrillate, and thus may be uneasy about doing so. Concerns about competence are exacerbated if training is infrequent, leading the caregiver to worry that he or she may not be able to remember all of the recommended resuscitation protocol steps and/or their correct sequence.

Similarly, both medical and lay caregivers may be hesitant to provide CPR and rescue breathing, or may be unsure when these steps should be performed, particularly if their training is infrequent and they rarely have the opportunity to use it.

It is well known to those skilled in the art, and has been shown in a number of studies, that CPR is a complex task with both poor initial learning as well as poor skill retention, with trainees often losing 80% of their initial skills within 6-9 months. It has thus been the object of a variety of prior art to attempt to improve on this disadvantageous condition. Aids in the performance of chest compressions are described in U.S. Pat. Nos. 4,019,501, 4,077,400, 4,095,590, 5,496, 257, 6,125,299, and 6,306,107, 6,390,996. U.S. Pat. Nos. 4,588,383, 5,662,690, 5,913,685, 4,863,385 describe CPR prompting systems AEDs have always included voice prompts as well as graphical instructions on flip charts or placards since the earliest commercial versions in 1974 to provide both correct timing and sequence for the complex series of actions required of the rescuer (caregiver) as well as placement of the defibrillation electrodes. U.S. patent application Ser. No. 09/952,834 and U.S. Pat. Nos. 6,334, 070 and 6,356,785 describe defibrillators with an increased level of prompting including visual prompts either in the form of graphical instructions presented on a CRT or on printed labels with backlighting or emissive indicia such as light emitting diodes AEDs since the 1970s have used the impedance measured between the defibrillation electrodes to determine the state of the AED as well as appropriate messages to deliver to the rescuer (e.g. "Attach Electrodes" if the initial prompts on the unit have been delivered and the impedance remains greater than some specified threshold) or to determine if there is excessive patient motion (as in U.S. Pat. No. 4,610,254.) U.S. Pat. No. 5,700,281 describes a device which uses the impedance of the electrodes to determine the state of the AED for delivering messages such as "Attach Electrodes". Enhanced prompting disclosed in these patents provides some benefit to the rescuer in improved adherence to the complex protocol required of them to successfully revive a cardiac arrest patient, but the enhanced prompting is usually not sufficient in real world situations. U.S. Pat. Nos. 5,662,690 and 6,356,785 (and the commercially available OnSite defibrillator) attempts to improve prompting by providing a rescuer-accessible "Help" key that initiates more detailed prompting in cases in which the rescuer or test subject is confused. But testing has shown that with the heightened level of anxiety that accompanies a real cardiac arrest, rescuers rarely remember to press such a Help key. Even notifying the rescuer at the beginning of the protocol to press the Help key does not help a the confused rescuer press the Help key. Furthermore, even if the Help key is pressed, it is necessary to have the rescuer work through a series of user interface interactions via a touchscreen, softkeys or other input means, for the help software to determine at which step the rescuer is in need of additional instructions. Putting the user through these interactions with the help software detracts from the rescuer's ability to provide aid to the patient, and thus delays delivery of therapy.

AEDs have also been solely focused on defibrillation, which, while it provides the best treatment for ventricular fibrillation and certain tachycardias, is of no therapeutic benefit for the 60% of the cardiac arrest patients presenting in pulseless electrical activity (PEA) or asystole. As AEDs are becoming more prevalent in the home, there are also a host of other health problems that occur such as first aid as well as incidents related to chronic conditions such as asthma, diabetes or cardiac-related conditions for which the AED is of no benefit.

It has been found in several clinical studies that supposedly trained personnel such as physicians, nurses, and paramedics trained in advanced cardiac life support (ACLS) do not provide optimal cardiac compressions, either with respect to rate or depth of compressions. This group of caregivers has also been shown in studies to provide ventilations at an excessive rate. Over-ventilation has been shown to result in excessive intra-thoracic pressure, which impedes the diastolic filling cycle and reduces blood flow and coronary and brain perfusion pressures during CPR. European Patent EP 1157717B1 and U.S. Pat. No. 6,821,254 describe systems for determining ventilation rates from an AC, small-signal transthoracic impedance (TTI) measured between the defibrillation electrode pads. A known limitation of this measurement method is the excessive noise present on the TTI signal due to a variety of noise sources, including body movement, capacitive fluctuations, and electrolyte charge transfer during chest compressions. Advanced caregivers also desire an accurate measure of "tidal volume"—the actual volume of gas transferred in and out of the lungs—to better assess the care provided and to make appropriate clinical decisions. Ventilation measurement based solely on TTI is, however, incapable of providing accurate measurements of tidal volume, unless an inconvenient initial calibration procedure is performed, due to the normal random inter-patient anatomical variations.

SUMMARY

In a first aspect, the invention features a device for assisting a caregiver in delivering cardiac resuscitation to a patient, the device comprising a user interface configured to deliver prompts to a caregiver to assist the caregiver in delivering cardiac resuscitation to a patient, at least one sensor configured to detect the caregiver's progress in delivering the cardiac resuscitation, wherein the sensor is configured to provide a signal containing information indicative of ventilation, a memory in which a plurality of different prompts are stored, including at least one ventilation progress prompt to guide the rescuer's performance of ventilation, a processor configured to process the output of the sensor to determine a parameter descriptive of ventilation progress and to determine whether the ventilation progress prompt should be selected for delivery.

Preferred implementations of this aspect of the invention may incorporate one or more of the following. The parameter descriptive of ventilation progress may be ventilation rate, and the ventilation progress prompt may comprise an instruction pertaining to varying the ventilation rate. The parameter descriptive of ventilation progress may be delivered tidal volume, and the ventilation progress prompt may comprise an instruction pertaining to varying the delivered tidal volume. The parameter descriptive of ventilation progress may be flow rate, and the ventilation progress prompt may comprise an instruction pertaining to varying the flow rate. The sensor may comprise an accelerometer, and the processor may process the output of the accelerometer to distinguish between ventilations and chest compressions. The sensor may comprise a pressure sensor, and the processor may process the output of the pressure sensor to determine the parameter descriptive of ventilation progress. There may be a plurality of other sensors configured to detect the caregiver's progress in delivering the cardiac resuscitation, wherein each of the plurality of sensor may be other than an electrode connected to the body. The processor may be configured to vary the time at which prompts are delivered based on the progress detected by the sensor. The device further may comprise one or more additional sensors configured to detect the caregiver's progress in delivering the therapy, wherein the one or more additional sensors may comprise an electrode in electrical contact with the body. The processor may select a series of more detailed prompts for delivery to a user when progress is slower than a predetermined pace. The processor may be configured to slow down the rate at which prompts are delivered when progress is slower than a predetermined pace. The user interface may deliver at least some of the prompts as oral instructions to be heard by the caregiver. The user interface may deliver at least some of the prompts as visual instructions to be seen by the caregiver. The user interface may comprise an electronic display. The electronic display may provide a series of images. The device may further comprise an automatic external defibrillator. The oral prompts may be associated with a series of graphics and may be given sequentially to guide the caregiver through a sequence of steps. The visual prompts may be delivered as a series of graphics with the sequential illumination of light sources to guide the caregiver through the sequence of graphics. The device may further comprise a processing system that measures and records the times required for a user to complete a sequence of steps and/or sub-steps in a protocol, and, based on the measured times adjusts the rate of the prompting delivered. The adjusting may be based on a comparison of the measured times with a set of stored values.

In a second aspect, the invention features an automatic external defibrillation device for delivering defibrillation shocks to a patient and for assisting a caregiver in delivering cardiac resuscitation to the patient, the device comprising an electrode pad supporting at least one defibrillation electrode, the pad being configured to be adhesively applied to the chest of the patient, at least one pressure sensor configured to detect information relating to the caregiver's delivery of ventilations to the patient, wherein at least a portion of the pressure sensor is mounted on the electrode pad, a processor configured to process the output of the pressure sensor to determine a parameter descriptive of ventilation progress.

Preferred implementations of this aspect of the invention may incorporate one or more of the following. The parameter descriptive of ventilation progress may be ventilation rate, and the ventilation progress prompt may comprise an instruction pertaining to varying the ventilation rate. The parameter descriptive of ventilation progress may be delivered tidal volume, and the ventilation progress prompt may comprise an instruction pertaining to varying the delivered tidal volume. The parameter descriptive of ventilation progress may be flow rate, and the ventilation progress prompt may comprise an instruction pertaining to varying the flow rate. At least one tube may run from the pressure sensor on the electrode pad to an adapter configured to be positioned in the vicinity of the patient's mouth, and the tube and adapter may be configured so that a pressure associated with ventilations is conveyed through the tube to the pressure sensor on the electrode pad assembly. The device may further comprise a second tube running from the pressure sensor to the adapter, and the adapter and tubes may be configured to measure a differential pressure associated with ventilations. The device may further comprise at least one indicator light on the electrode pad assembly to convey information about delivered ventilations. The information may comprise whether ventilation rate is within a predetermined range of acceptable ventilation rates. The information may comprise an indication of the delivered tidal volume.

In a third aspect, the invention features a device for assisting a caregiver in delivering cardiac resuscitation to a patient, the device comprising a user interface configured to deliver prompts to a caregiver to assist the caregiver in delivering cardiac resuscitation to a patient, at least two sensors configured to provide signals from which information can be derived on the placement of an ET tube in the patient, a memory in which a plurality of different prompts are stored, including at least a first ET tube placement prompt providing a first indication as to the placement of the ET tube, a processor configured to process the outputs of the sensors to determine the ET tube placement and to determine whether the first ET tube placement prompt should be delivered.

Preferred implementations of this aspect of the invention may incorporate one or more of the following. The first ET tube placement prompt may comprise a prompt indicating that the ET tube is not correctly placed in the patient's trachea. The sensors may comprise a pressure sensor configured to detect the timing of ventilations delivered to the ET tube and an accelerometer may be configured to detect sternal motion in the patient. The sensors may comprise a pressure sensor configured to detect the timing of ventilations delivered to the ET tube and a TTI sensor may be configured to detect changes in the transthoracic impedance of the patient. One of the sensors may be configured to detect the timing of ventilations delivered to the ET tube, another of the sensors may be configured to detect the timing of sternal movement in the patient or of change in transthoracic impedance of the patient, and the processor may be configured to compare the relative timing of ventilations and sternal movements or transthoracic impedance changes.

Among the many advantages of the invention (some of which may be achieved only in some of its various aspects and implementations) are that the invention provides a more effective means of measuring ventilations. Accurate tidal volumes can conveniently be measured, and the ventilation measurements are more immune to noise.

Other features and advantages of the invention will be apparent from the description and drawings, and from the claims.

DESCRIPTION OF DRAWINGS

FIG. 1 is a perspective view of an AED with its cover on.

FIGS. 7a and 7b list the audio prompts used in the flowcharts shown in FIGS. 6a-6e.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

The terms "caregiver", "rescuer" and "user" are used interchangeably and refer to the operator of the device providing care to the patient.

Figure 1:
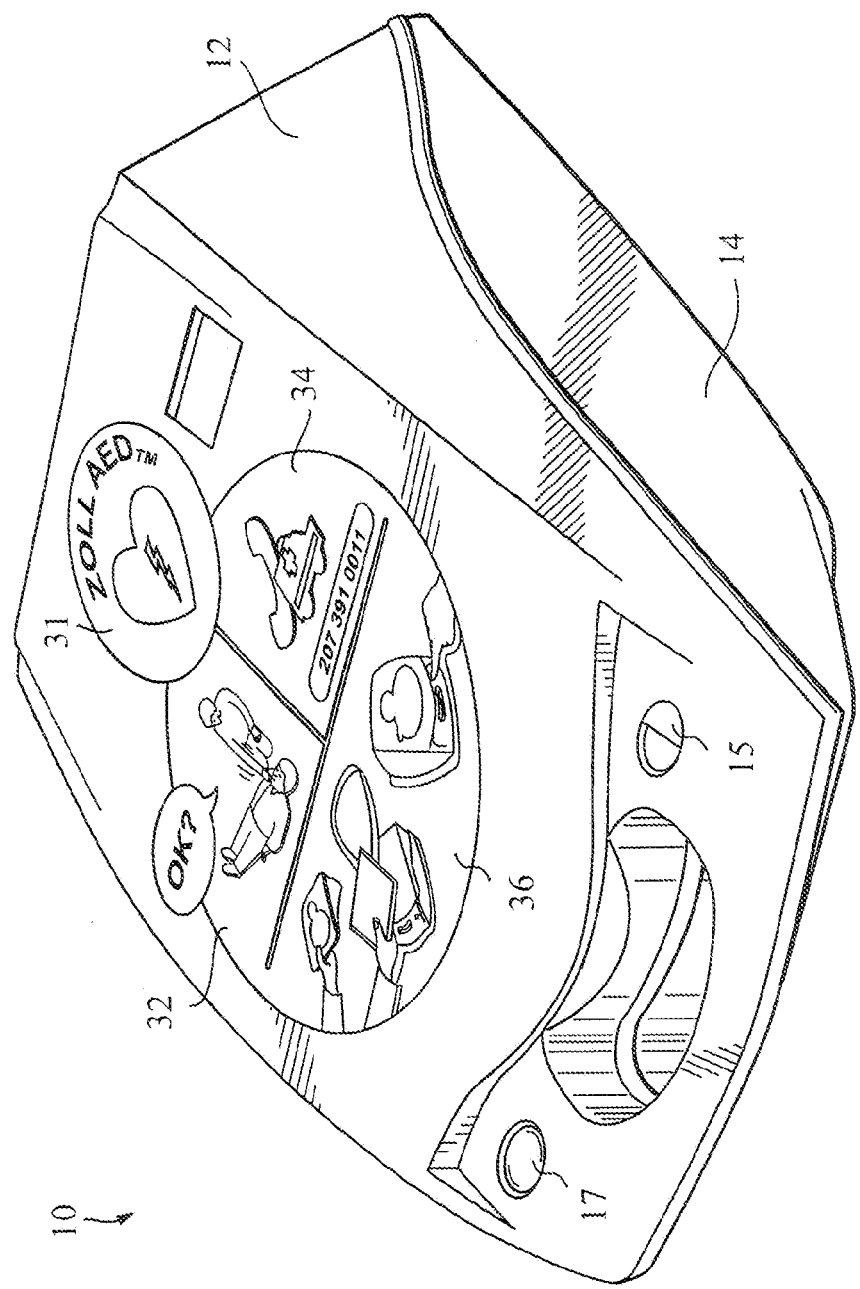
Figure 2:
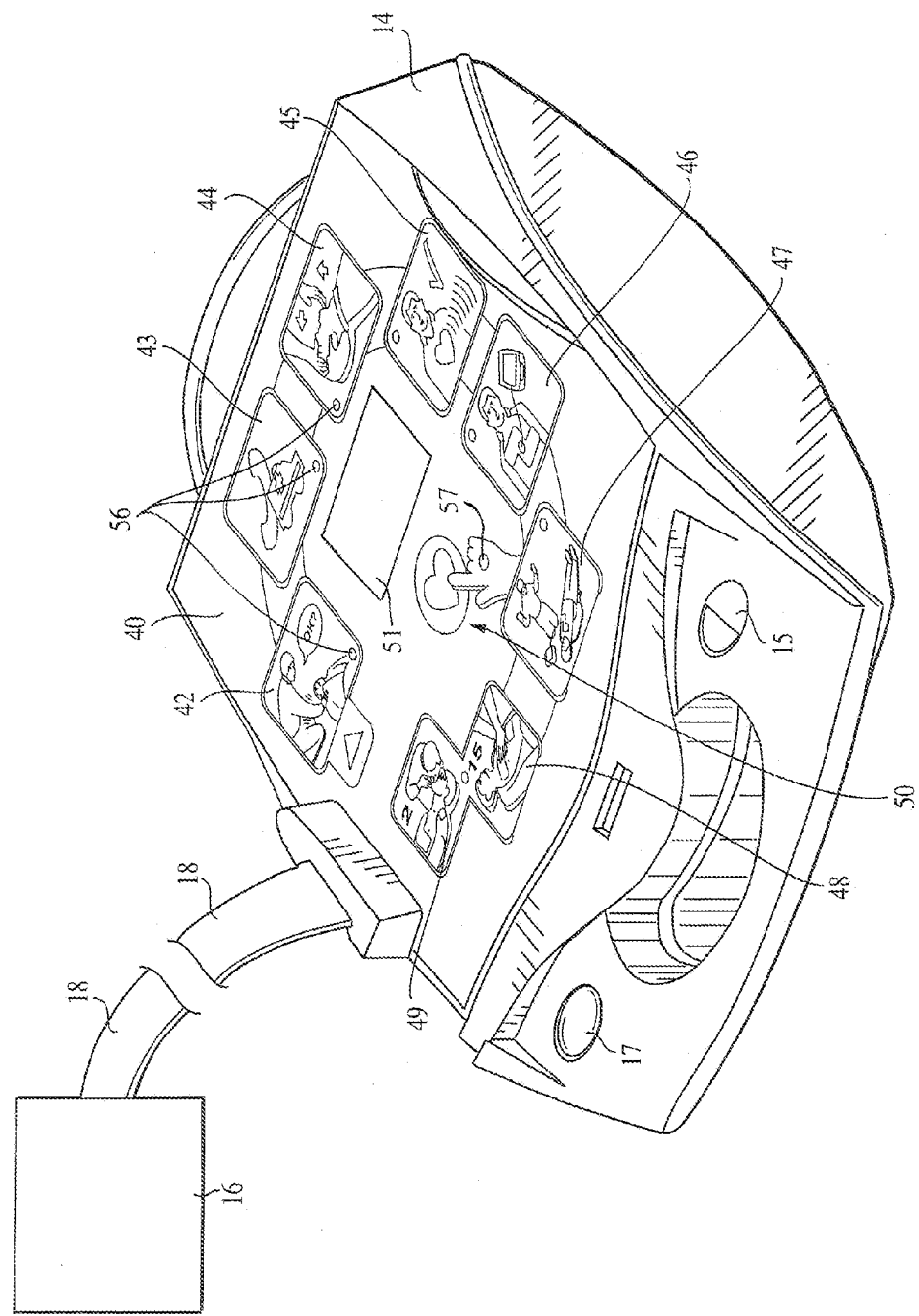
FIG. 2 is a perspective view of the AED of FIG. 1 with the cover removed.

Referring to FIGS. 1 and 2, an automated external defibrillator (AED) 10 includes a removable cover 12 and a device housing 14. The defibrillator 10 is shown with cover 12 removed in FIG. 2. An electrode assembly 16 (or a pair of separate electrodes) is connected to the device housing 14 by a cable 18. Electrode assembly 16 is stored under cover 12 when the defibrillator is not in use.

Figure 3:
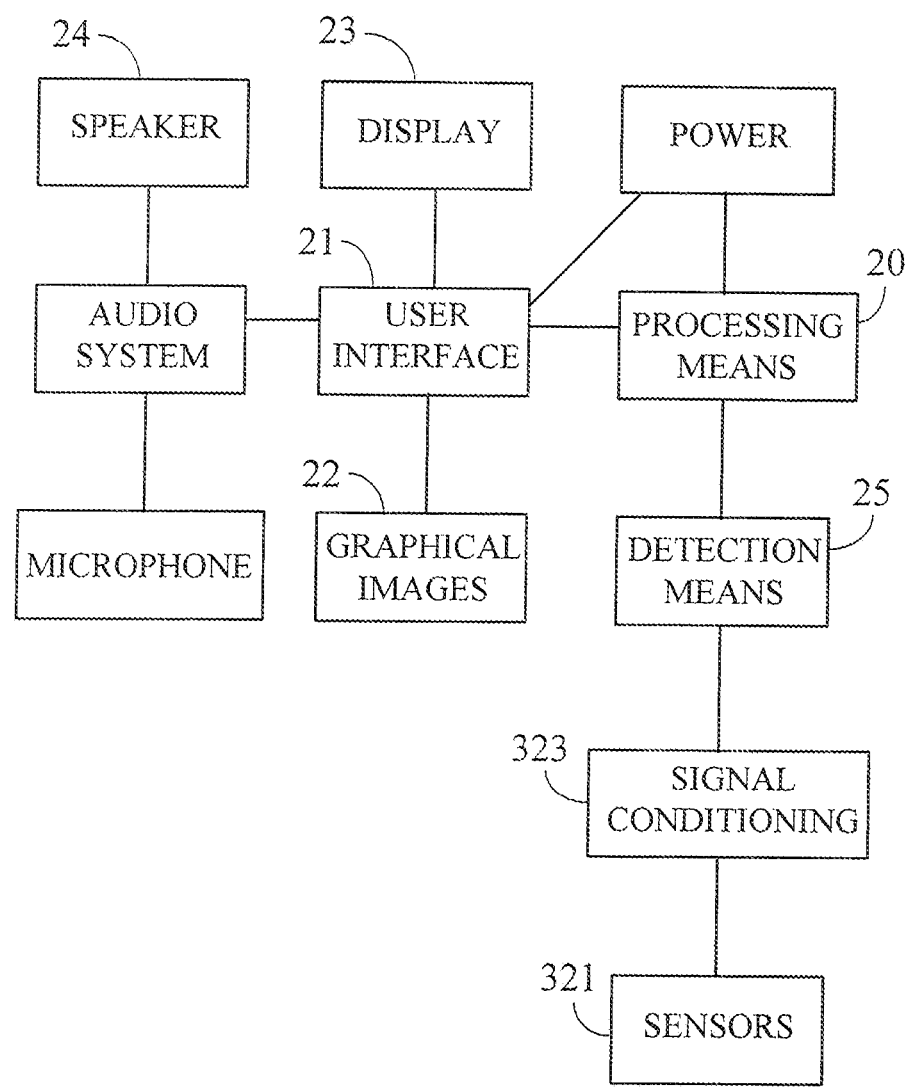
FIG. 3 is a block diagram of the AED.

Referring to FIG. 3, the AED includes circuitry and software 20 for processing, a user interface 21 including such elements as a graphical 22 or text display 23 or an audio output such as a speaker 24, and circuitry and/or software 25 for detecting a caregiver's progress in delivering therapy—e.g., detecting whether one or more of a series of steps in a protocol has been completed successfully. In some preferred implementations, the detecting also includes the ability to determine both whether a particular step has been initiated by a user and additionally whether that particular step has been successfully completed by a user. Based on usability studies in either simulated or actual use, common user errors are determined and specific detection means are provided for determining if the most prevalent errors have occurred.

If it is determined that the current step in the protocol has not been completed, then the processor will pause the currently-scheduled sequence of instructions. If, for instance, it has been determined that a particular step has been initiated but not completed, but none of the common errors has occurred subsequent to initiation of the particular step, then the processor may simply provide a pause while waiting for the user to complete the step. If, after waiting for a predetermined period of time based on prior usability tests, there has been no detection of the step completion, the processor may initiate a more detailed set of prompts, typically at a slower sequence rate, describing the individual sub-steps that comprise a particular step. If one of the common errors is detected while waiting for completion of the step, the processor may initiate a sequence of instructions to correct the user's faulty performance.

Device housing 14 includes a power button 15 and a status indicator 17. Status indicator 17 indicates to the caregiver whether the defibrillator is ready to use.

The cover 12 includes a cover decal 30 (FIG. 1) including a logo 31 and a series of graphics 32, 34 and 36. Logo 31 may provide information concerning the manufacturer of the device and that the device is a defibrillator (e.g., "ZOLL AED", as shown in FIG. 1, indicating that the device is a Semi-Automatic External Defibrillator available from Zoll Medical). Graphics 32, 34 and 36 lead the caregiver through the initial stages of a cardiac resuscitation sequence as outlined in the AHA's AED treatment algorithm for Emergency Cardiac Care pending arrival of emergency medical personnel. (See "Guidelines 2000 for Cardiopulmonary Resuscitation and Emergency Cardiovascular Care. Supplement to Circulation," Volume 102, Number 8, Aug. 22, 2000, pp. I-67.) Thus, graphic 32, showing the caregiver and patient, indicates that the caregiver should first check the patient for responsiveness, e.g., by shaking the patient gently and asking if the patient is okay. Next, graphic 34, showing a telephone and an emergency vehicle, indicates that the caregiver should call for emergency assistance prior to administering resuscitation. Finally, graphic 36 indicates that after these steps have been performed the caregiver should remove the cover 12 of the defibrillator, remove the electrode assembly 16 stored under the lid, and turn the power on by depressing button 15. The graphics are arranged in clockwise order, with the first step in the upper left, since this is the order most caregivers would intuitively follow. However, in this case the order in which the caregiver performs the steps is not critical, and thus for simplicity no other indication of the order of steps is provided.

The device housing includes a device housing decal 40, shown in FIG. 2. The graphics are configured to lead the caregiver through the entire resuscitation sequence, as will be explained below with reference to FIGS. 6a-6e. Decal 40 also includes a center graphic 50, which includes representations of a hand and a heart. Center graphic 50 overlies a treatment button which, when depressed, causes the defibrillator to deliver a defibrillating shock to the electrode assembly 16.

Each of the graphics on device housing decal 40 is accompanied by a light source that can be temporarily illuminated to indicate that the illuminated step should be performed at that particular time. These light sources guide the caregiver, step-by-step, through the resuscitation sequence, indicating which graphic should be viewed at each point in time during resuscitation.

The light source for each of the graphics 42-49 is preferably an adjacent LED (LEDs 56, FIG. 2). The heart may be translucent and backlit by a light source in the device housing (not shown). Alternatively, the heart may include an adjacent LED (not shown) and/or the hand may include an LED 57 as shown. Programmable electronics within the device housing 14 are used to determine when each of the light sources should be illuminated.

In some preferred implementations, a liquid crystal display 51 is used to provide the more detailed graphical prompts when a user is unable to complete the rescue sequence on their own. In these implementations, the purpose of the printed graphics is to provide a more general indication of the current step in the overall sequence, e.g. airway graphics 44 provides an indication that the rescuer should be performing the "Open Airway. Check for Breathing." sub-sequence, but may not provide a detailed enough description for someone who has forgotten the correct actions to perform. In an alternative embodiment, the graphical instructions may be provided by a larger version of the liquid crystal display (LCD) 51 whereby the LED-lit printed instructions are eliminated or removed and most or all of the graphical instructions are provided by the LCD 30. In this case, the LCD 51 will automatically show the more detailed instructions when it determines that the user is unable to properly perform the action.

The programmable electronics may also provide audio prompts, timed to coincide with the illumination of the light sources and display of images on the liquid crystal display 51, as will also be discussed below with reference to FIGS. 6*a* and 6*e*.

Figure 10A:
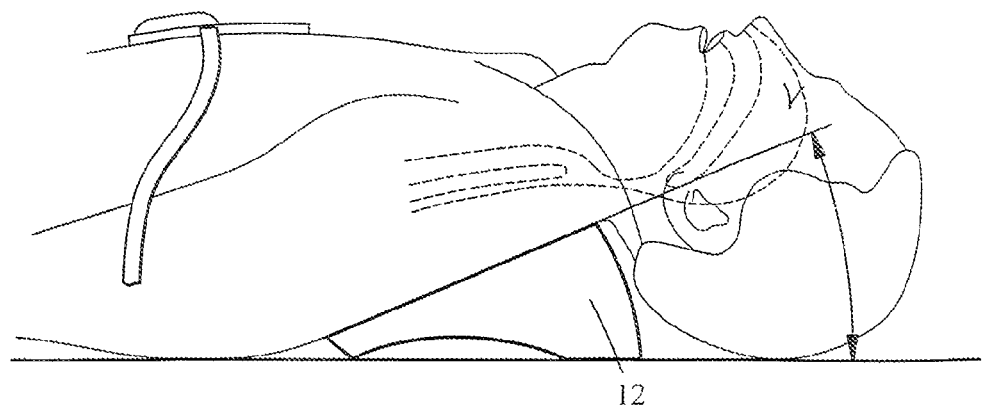
FIGS. 10a and 10b are side views of a patient with and without the cover placed beneath the shoulders, to show the effect on the patient's airway of placing the cover beneath the shoulders.
Figure 10B:
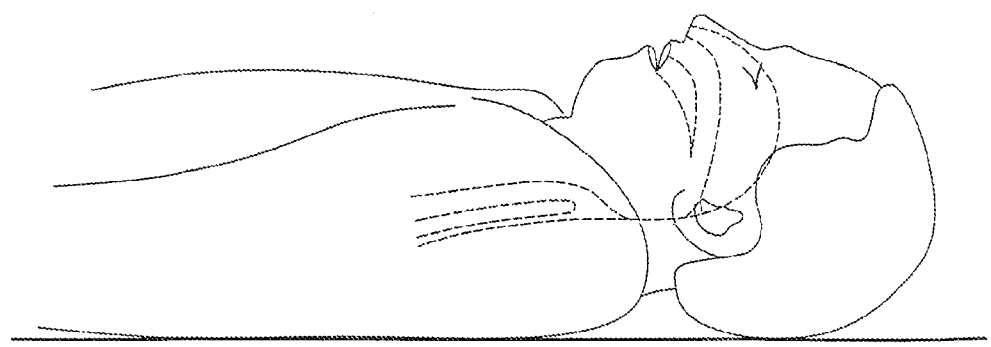

The cover 12 is constructed to be positioned under a patient's neck and shoulders, as shown in FIGS. 10*a* and 10*b*, to support the patient's shoulders and neck in a way that helps to maintain his airway in an open position, i.e., maintaining the patient in the head tuck-chin lift position. The cover is preferably formed of a relatively rigid plastic with sufficient wall thickness to provide firm support during resuscitation. Suitable plastics include, for example, ABS, polypropylene, and ABS/polypropylene blends.

Prior to administering treatment for cardiac arrest, the caregiver should make sure that the patient's airway is clear and unobstructed, to assure passage of air into the lungs. To prevent obstruction of the airway by the patient's tongue and epiglottis (e.g., as shown in FIG. 10*a*), it is desirable that the patient be put in a position in which the neck is supported in an elevated position with the head tilted back and down. Positioning the patient in this manner is referred to in the American Heart Association Guidelines for Cardiopulmonary Resuscitation and Emergency Cardiovascular Care as the "head tilt-chin lift maneuver." The head tilt-chin lift position provides a relatively straight, open airway to the lungs through the mouth and trachea. However, it may be difficult to maintain the patient in this position during emergency treatment.

The cover 12 has an upper surface 24 that is inclined at an angle A (FIG. 9*a*) of from about 10 to 25 degrees, e.g., 15 to 20 degrees, so as to lift the patient's shoulders and thereby cause the patient's head to tilt back. The upper surface 24 is smoothly curved to facilitate positioning of the patient. A curved surface, e.g., having a radius of curvature of from about 20 to 30 inches, generally provides better positioning than a flat surface. At its highest point, the cover 12 has a height H (FIG. 9) of from about 7.5 to 10 cm. To accommodate the width of most patients' shoulders, the cover 12 preferably has a width W (FIG. 9) of at least 6 inches, e.g., from about 6 to 10 inches. If the cover 12 is not wide enough, the patient's neck and shoulders may move around during chest compressions, reducing the effectiveness of the device. The edge of the cover may also include a lip 11 (FIG. 9) or gasket (not shown) to prevent water from entering the housing when the cover is in place. The positions shown in FIGS. 10*a* and 10*b* (a patient in the head lift-chin tilt position and a patient with a closed airway) are also shown in the AHA Guidelines for Cardiopulmonary Resuscitation and Emergency Cardiovascular Care, Aug. 22, 2000, p. 1-32, FIGS. 7 and 8.

Figure 8:
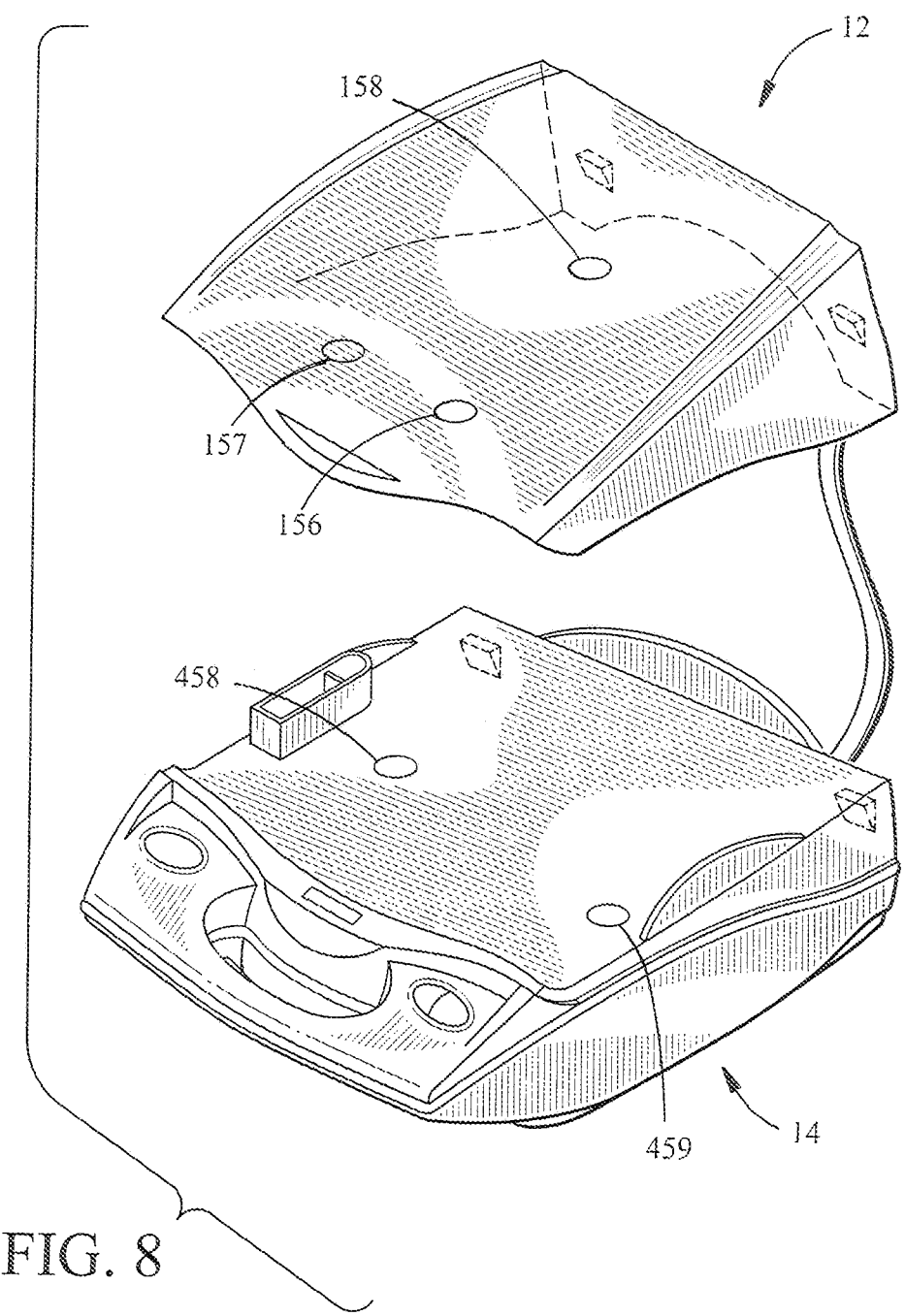
FIG. 8 is an exploded perspective view of the cover and housing.
Figure 9:
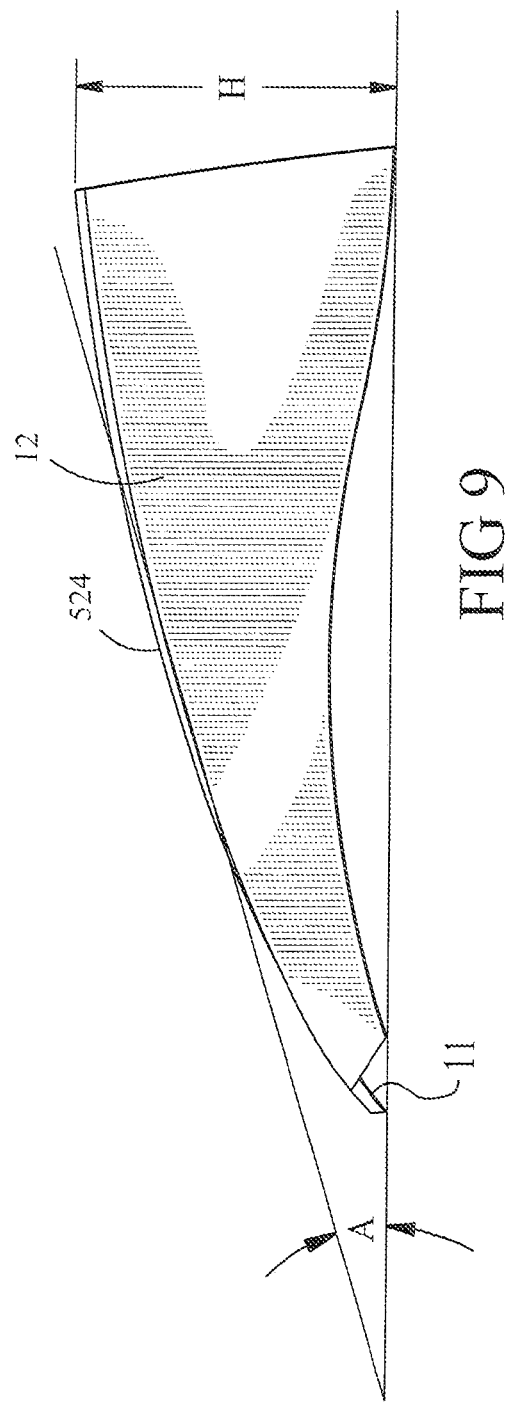
FIG. 9 is a side plan view of the cover indicating angle 'A'.

The cover 12 is provided with one or more sensors for determining if the patient's shoulders have been properly positioned on the cover 12. Referring to FIG. 8, two photoelectric sensors 156, 157 are used to determine if the cover has been placed underneath the patient's back. The sensors 156, 157 are located along the acute edge of the cover 12, with one facing inward and one facing outward with the cable 155 providing both power to the sensors 156, 157 as well as detection of the sensor output. If the cover 12 is upside down, the inner sensor 156 will measure a higher light level than the outer sensor 157; if the cover has been placed with the acute edge facing toward the top of the patient's head, then the outer sensor 157 will measure higher than the inner sensor 156 and will also exceed a pre-specified level. In the case of a properly positioned cover, both inner 156 and outer sensor 157 outputs will be below a pre-specified level. In another embodiment, the detections means is provided by a pressure sensor 158 located underneath the cover decal. Referring to FIG. 6*c*, if the processing means 20 detects that the cover is upside down 153, it will cause an audible prompt 151 to be delivered to the user that is more detailed than the original prompt. The processing means 20 will also slow down the rate of speech of the audio prompts. If the cover is still upside down after a predetermined period of time, the processing means 20 will deliver an even more detailed message on how to properly place the cover. If, after three attempts to get the user to properly position the cover 12, the processing means 20 will deliver the next audio prompt 160 without further waiting for proper placement of the cover 12.

In the preferred embodiment, the defibrillator includes communication capability such as cell phone, global positioning system (GPS) or simpler wireless phone capability. Preferably, both cell phone and GPS are included in the device. The cell phone is preconfigured to automatically dial the Emergency Response Center (ERC) in the community in which it is located such as "911" in much of the United States. The cell phone service is chosen which is able to provide voice, data, as well as GPS capability. Thus in response to a command by the device to "Call 911 by Pressing the Phone button", the device automatically dials 911 and the built-in speaker 158 and microphone 159 on the device function to provide speakerphone capability. If a connection is successfully made to the emergency response center, the device transmits its exact location based on its GPS capability and also can transmit to the response center the status of the defibrillator. In more advanced modes, the emergency response center can remotely control the operation of the defibrillator via the bi-directional data capability. When a connection is made to the ERC and emergency response personnel (ERP), the automatic voice prompting of the defibrillator can be remotely de-activated by the ERP so as not to distract the rescuer from the instructions given by the ERP. While coaching the rescuer via the speakerphone capability in the defibrillator, the ERP can utilize the responsive feedback prompting functionality of the device to provide more accurate coaching of the rescuer. It is well known, however, that cell phone and other wireless communication methods are not especially reliable even under the best circumstances, and are often completely unavailable in industrial facilities, basements, etc., thus it is important to provide a means of automatically reverting to the mode wherein the device provides all responsive feedback prompts to the user when the processor detects that the communication link has been lost. Additional prompts will also be provided to the user to assuage any concern they might have that the connection to the human expert has been lost (e.g. "Communication has been temporarily lost to 911 personnel. Don't worry. This AED is able to perform all steps and help you through this procedure."). When a communication link has been lost, the device will preferably automatically begin recording all device and patient status as well as all audio received by the built-in microphone. If the communication link is subsequently reacquired, the device will preferably automatically transmit the complete event, including patient, device and audio data, acquired during the time communication was not available, providing ERP valuable data to help in their medical decision-making. The ERP may remotely control the defibrillator via a bi-directional communication link that transmits both voice and data.

In another embodiment, a remote computer located at the ERC, that is more capable than the processor in the device may provide the remote decision-making capability. The remote computer would run artificial intelligence software utilizing such techniques, e.g., as fuzzy logic, neural nets and intelligent agents to provide prompting to the user.

Figure 6A:
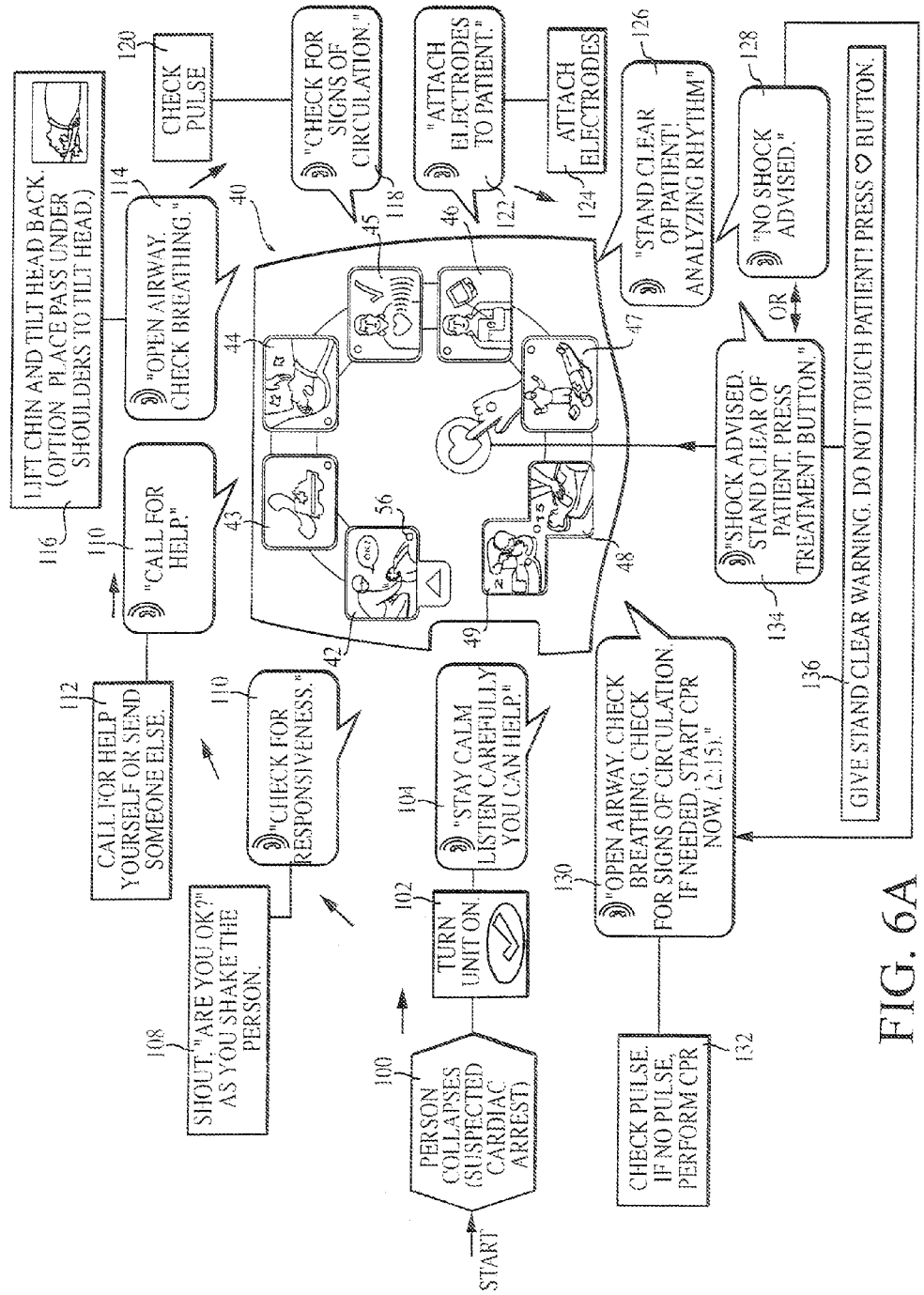
FIG. 6a-6e are flow charts indicating audio prompts provided during use of the AED of FIG. 1 and steps to be performed by the caregiver in response to the graphical and audio prompts.
Figure 6B:
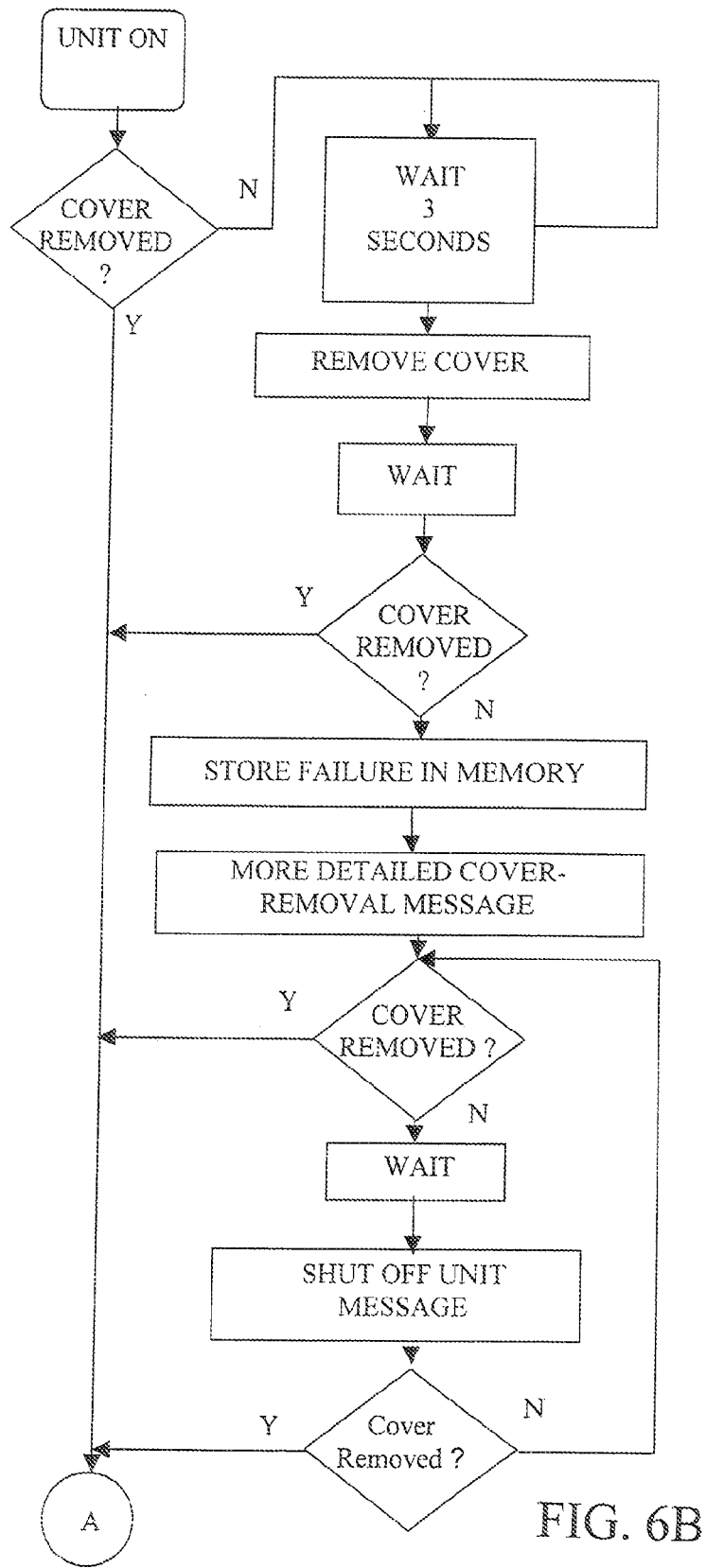
Figure 6C:
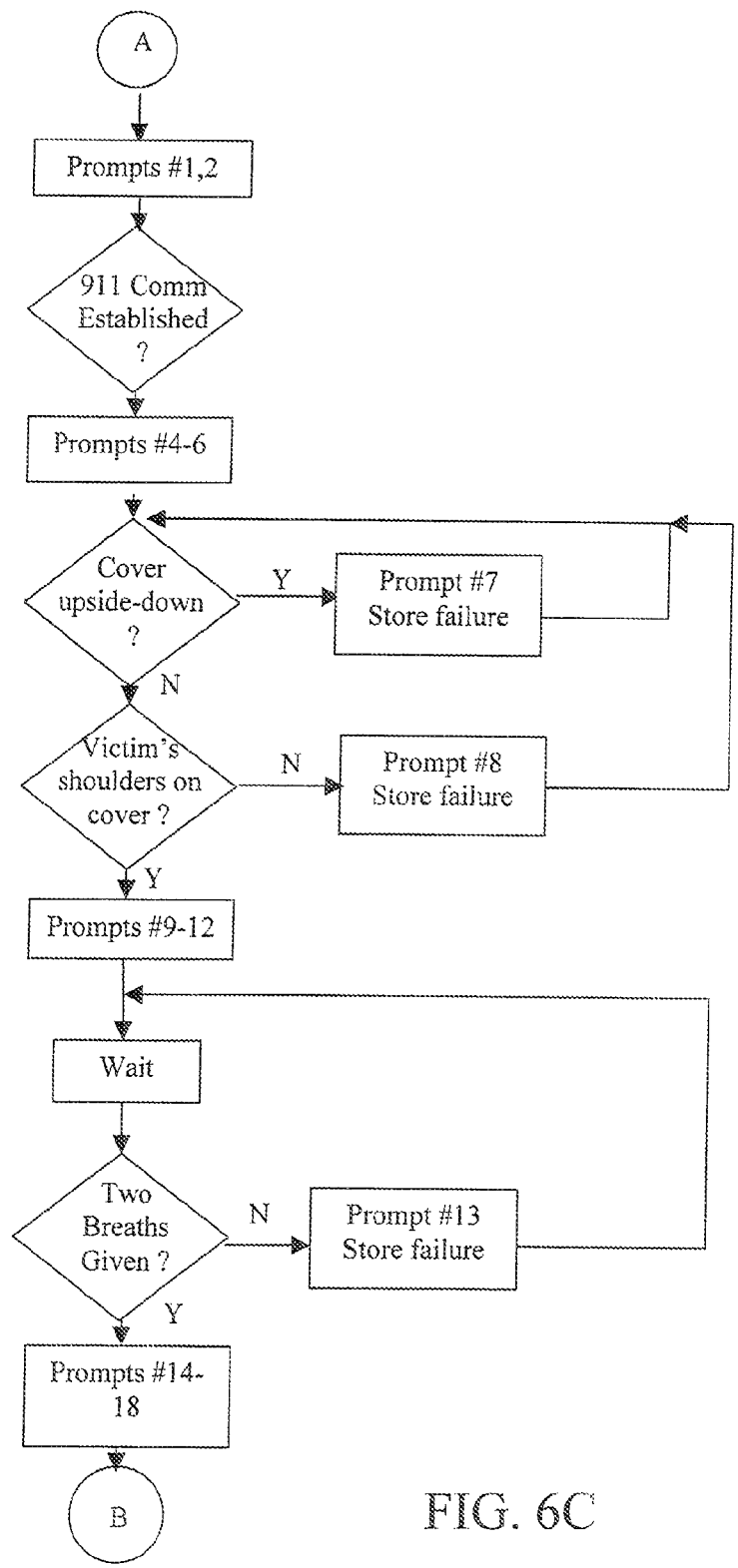
Figure 6D:
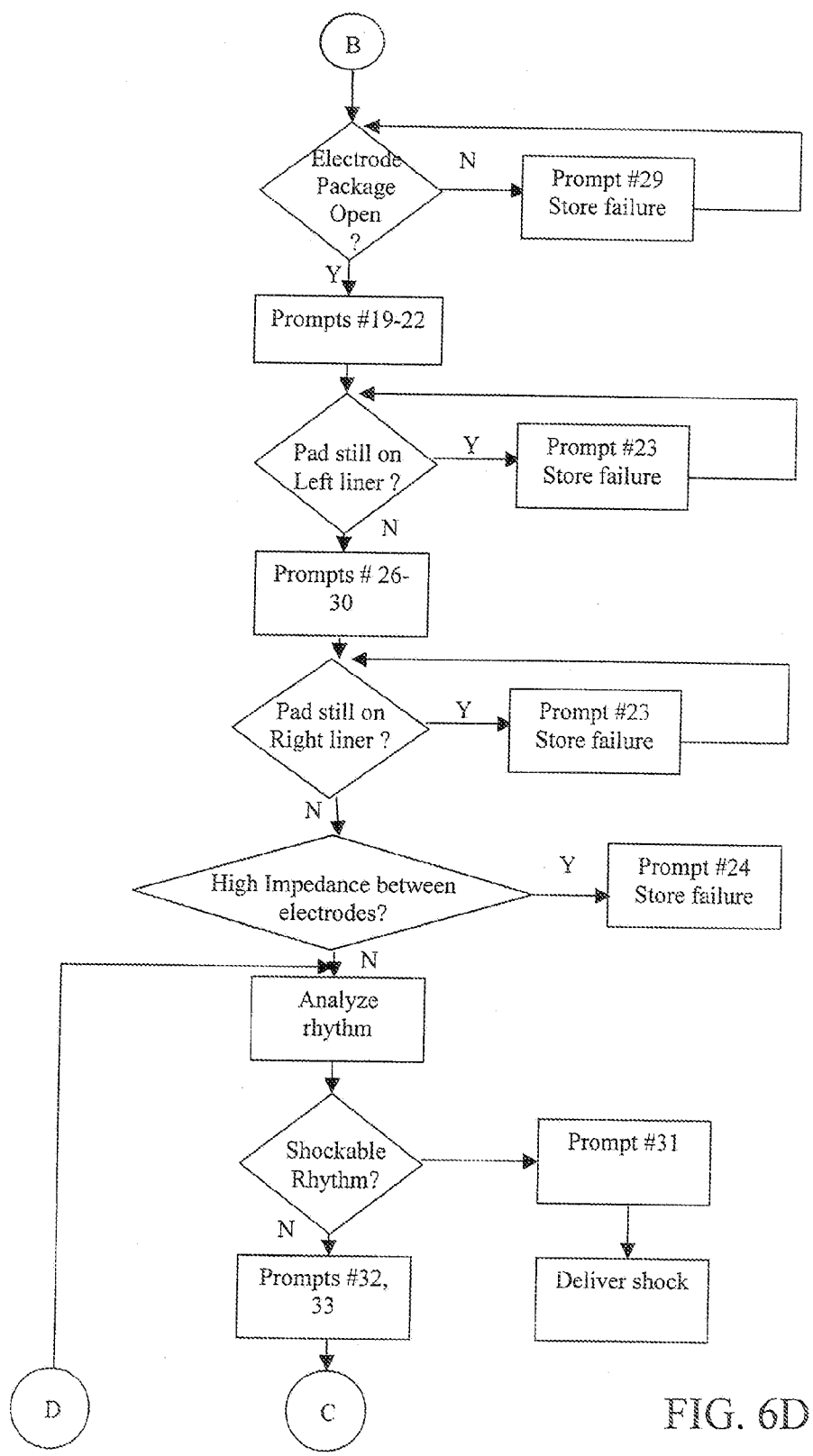
Figure 6E:
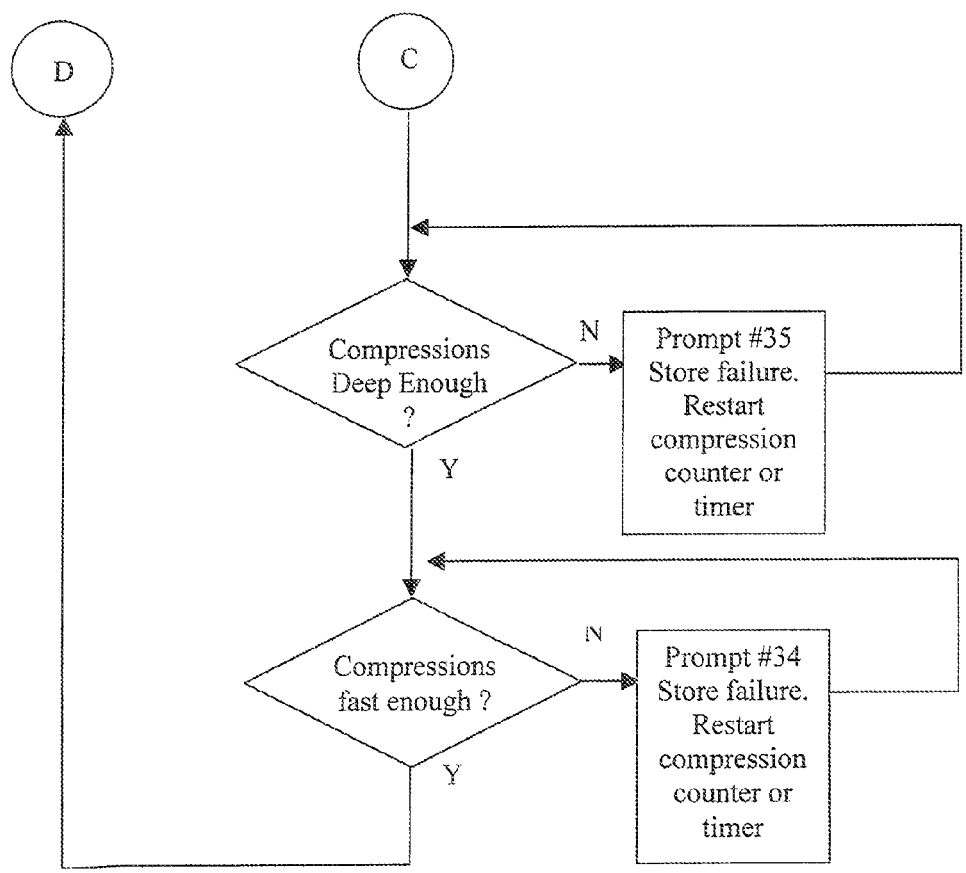

FIG. 6a illustrates, in flow chart form, the default graphical and audio prompts provided by the device for a caregiver performing resuscitation. The prompts shown in the figure do not include responsive feedback prompts by the device that provide more detailed instructions depending on whether particular sequences have been successfully completed by the caregiver. The text in boxes indicates steps performed by the caregiver. The text in caption balloons, with ear symbols, indicates audio prompts generated by the defibrillator. FIGS. 6b-6e provide flowcharts of more detailed responsive feedback prompts (the content of which are shown in FIGS. 7a, 7b) that may be provided to supplement the steps of calling for help, open airway/check for breathing, and defibrillation electrode application.

Thus, when a person collapses and a caregiver suspects that the person is in cardiac arrest 100, the caregiver first gets the defibrillator and turns the power on 102. If the unit passes its internal self tests, and is ready for use, this will be indicated by indicator 17, as discussed above. Next, the defibrillator prompts the caregiver with an introductory audio message, e.g., "Stay calm. Listen carefully." (Audio prompt 104.)

Shortly thereafter, the defibrillator will prompt the caregiver with an audio message indicating that the caregiver should check the patient for responsiveness (audio prompt 106). Simultaneously, the LED adjacent graphic 42 will light up, directing the caregiver to look at this graphic. Graphic 42 will indicate to the caregiver that she should shout "are you OK?" and shake the person (step 108) in order to determine whether the patient is unconscious or not.

After a suitable period of time has elapsed (e.g., 2 seconds), if the caregiver has not turned the defibrillator power off (as would occur if the patient were responsive), the defibrillator will give an audio prompt indicating that the caregiver should call for help (audio prompt 110). Simultaneously, the LED adjacent graphic 42 will turn off and the LED adjacent graphic 43 will light up, directing the caregiver's attention to graphic 43. Graphic 43 will remind the caregiver to call emergency personnel (step 112), if the caregiver has not already done so.

After a suitable interval has been allowed for the caregiver to perform step 112 (e.g., 2 seconds since audio prompt 110) the defibrillator will give an audio prompt indicating that the caregiver should open the patient's airway and check whether the patient is breathing (audio prompt 114). The LED adjacent graphic 43 will turn off, and the LED adjacent graphic 44 will light up, directing the caregiver's attention to graphic 44, which shows the proper procedure for opening a patient's airway. This will lead the caregiver to lift the patient's chin and tilt the patient's head back (step 116). The caregiver may also position an airway support device under the patient's neck and shoulders, if desired, as discussed below with reference to FIGS. 10a, 10b. The caregiver will then check to determine whether the patient is breathing.

After a suitable interval (e.g., 15 seconds since audio prompt 114), the defibrillator will give an audio prompt indicating that the caregiver should check for signs of circulation (audio prompt 118), the LED adjacent graphic 44 will turn off, and the LED adjacent graphic 45 will light up. Graphic 45 will indicate to the caregiver that the patient should be checked for a pulse or other signs of circulation as recommended by the AHA for lay rescuers (step 120).

After a suitable interval (e.g., 5 to 7 seconds since audio prompt 118), the defibrillator will give an audio prompt indicating that the caregiver should attach electrode assembly 16 to the patient (audio prompt 122), the LED adjacent graphic 45 will turn off, and the LED adjacent graphic 46 will light up. Graphic 46 will indicate to the caregiver how the electrode assembly 16 should be positioned on the patient's chest (step 124).

At this point, the LED adjacent graphic 47 will light up, and the defibrillator will give an audio prompt indicating that the patient's heart rhythm is being analyzed by the defibrillator and the caregiver should stand clear (audio prompt 126). While this LED is lit, the defibrillator will acquire ECG data from the electrode assembly, and analyze the data to determine whether the patient's heart rhythm is shockable. This analysis is conventionally performed by AEDs.

If the defibrillator determines that the patient's heart rhythm is not shockable, the defibrillator will give an audio prompt such as "No shock advised" (audio prompt 128). The LEDs next to graphics 48 and 49 will then light up, and the defibrillator will give an audio prompt indicating that the caregiver should again open the patient's airway, check for breathing and a pulse, and, if no pulse is detected by the caregiver, then commence giving CPR (audio prompt 130, step 132). Graphics 48 and 49 will remind the caregiver of the appropriate steps to perform when giving CPR.

Alternatively, if the defibrillator determines that the patient's heart rhythm is shockable, the defibrillator will give an audio prompt such as "Shock advised. Stand clear of patient. Press treatment button." (Audio prompt 134.) At the same time, the heart and/or hand will light up, indicating to the caregiver the location of the treatment button. At this point, the caregiver will stand clear (and warn others, if present, to stand clear) and will press the heart, depressing the treatment button and administering a defibrillating shock (or a series of shocks, as determined by the defibrillator electronics) to the patient (step 136).

After step 136 has been performed, the defibrillator will automatically reanalyze the patient's heart rhythm, during which audio prompt 126 will again be given and graphic 47 will again be illuminated. The analyze and shock sequence described above will be repeated up to three times if a shockable rhythm is repeatedly detected or until the defibrillator is turned off or the electrodes are removed. After the third shock has been delivered, the device will illuminate LEDs 48 and 49 and issue the audio prompts 130/132. The device will keep LEDs 48 and 49 illuminated for a period of approximately one minute indicating that if CPR is performed, it should be continued for the entire minute. "Continue CPR" audio prompts may be repeated every 15-20 seconds during this period to instruct the user to continue performing chest compressions and rescue breathing.

After approximately one minute has elapsed, the device will extinguish LEDs 48 and 49 and illuminate LED 47. Audio prompt 126 (stand clear, analyzing rhythm) will also be issued and a new sequence of up to three ECG analyses/shocks will begin.

If the caregiver detects circulation during step 132, the caregiver may turn off the defibrillator and/or remove the electrodes. Alternatively, the caregiver may not perform further CPR, but nonetheless allow the device to reanalyze the ECG after each one minute CPR period in order to provide repeated periodic monitoring to ensure the patient continues to have a non-shockable rhythm.

Thus, in the continuing presence of a shockable rhythm, the sequence of three ECG analyses and three shocks, followed by one minute of CPR, will continue indefinitely. If, instead, a non-shockable rhythm is or becomes present, the sequence will be analyze/no shock advised, one minute of CPR, analyze/no shock advised, one minute of CPR, etc. When a shock is effective in converting the patient's heart rhythm to a heart rhythm that does not require further defibrillating treatment, the sequence will be: analyze/shock advised, shock (saves patient), analyze/no shock advised, one minute CPR period (if pulse is detected then caregiver will not do CPR during this period), analyze/no shock advised, one minute CPR period, etc., continuing until the caregiver turns the defibrillator (e.g., if the caregiver detects a pulse) or the electrodes are removed.

Figure 14:
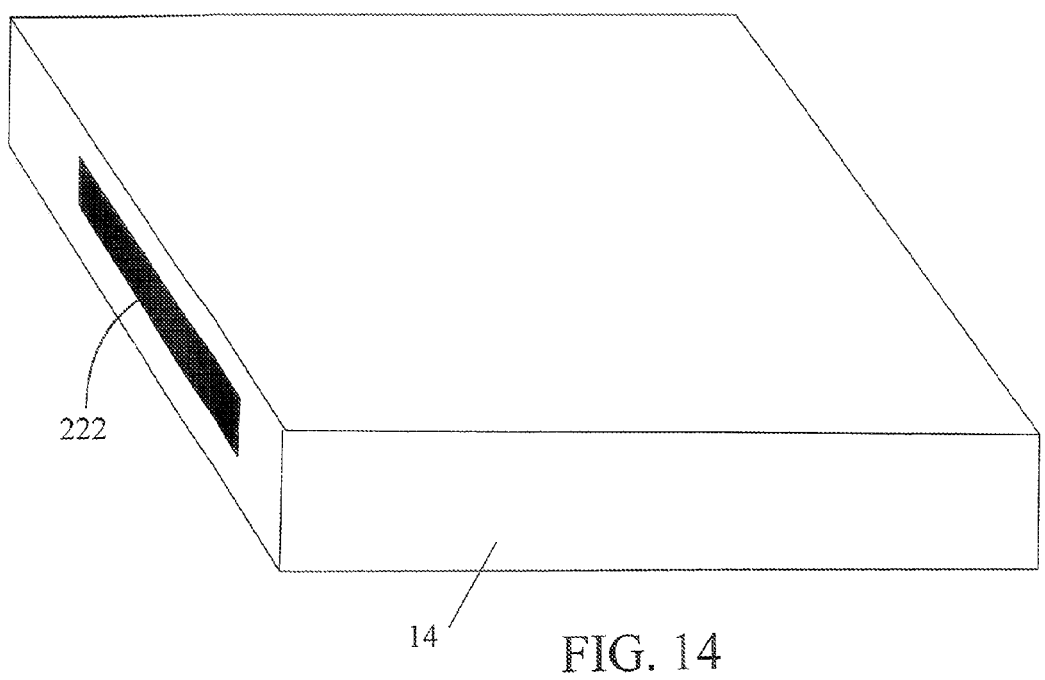
FIG. 14 is an isometric view of an electrode well along one side of the housing.
Figure 15:
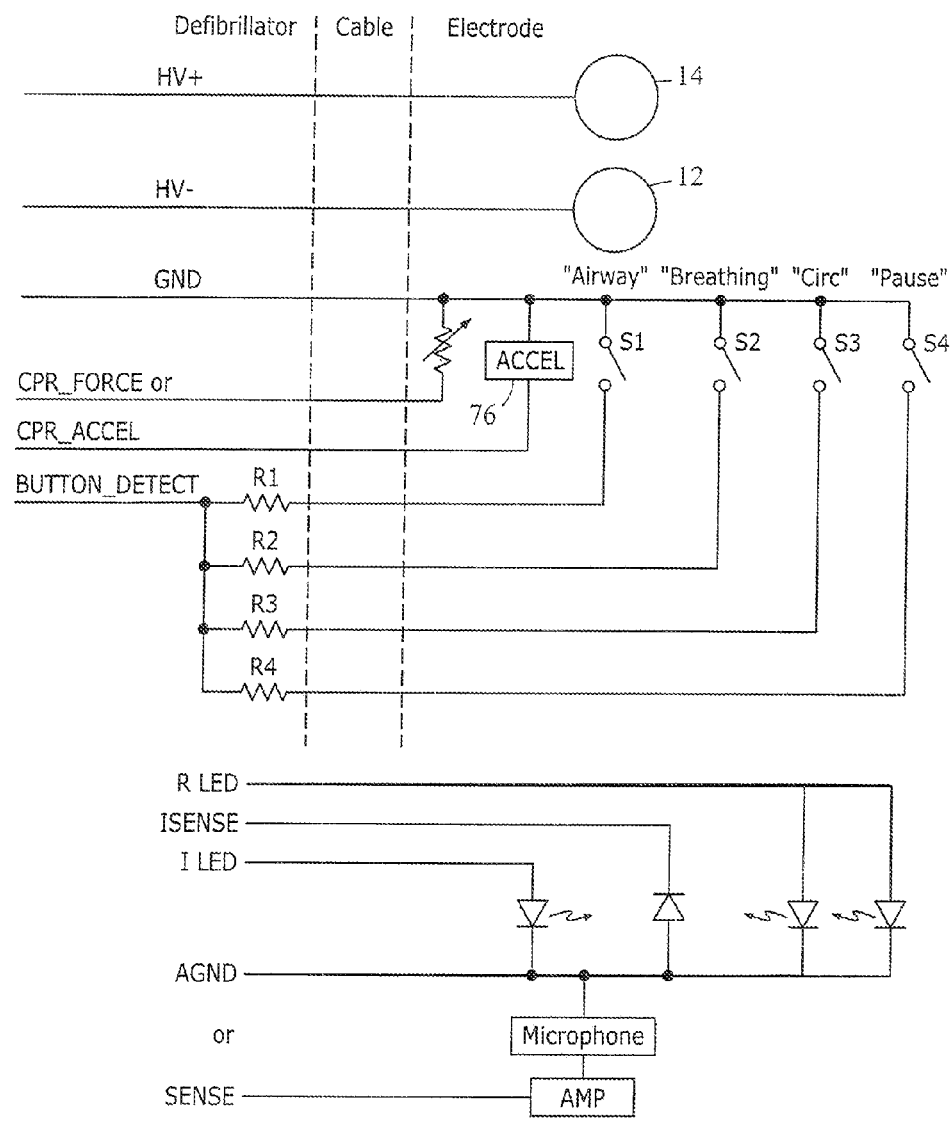
FIG. 15 is a schematic of the electronics contained in the integrated electrode pad of FIG. 12.

If electrode contact is lost at any time (as determined by the impedance data received from the electrode assembly), this will result in an appropriate audio prompt, such as "check electrodes" and illumination of the LED adjacent graphic 46. The electrodes 212, 214 may be stored in a well 222 (FIG. 14) that is structurally integrated with the housing 14 or may be a separate pouch 16.

It has also been discovered that a not-insignificant portion of caregivers are unable to open the packaging for the electrodes; therefore, a sesnor may be provided to determine if the electrode package has been opened. If detection of the electrode package 16 opening has not occurred within a predetermined period of time, the unit will provide more detailed instructions to assist the user in opening the packaging 16.

Figure 12:
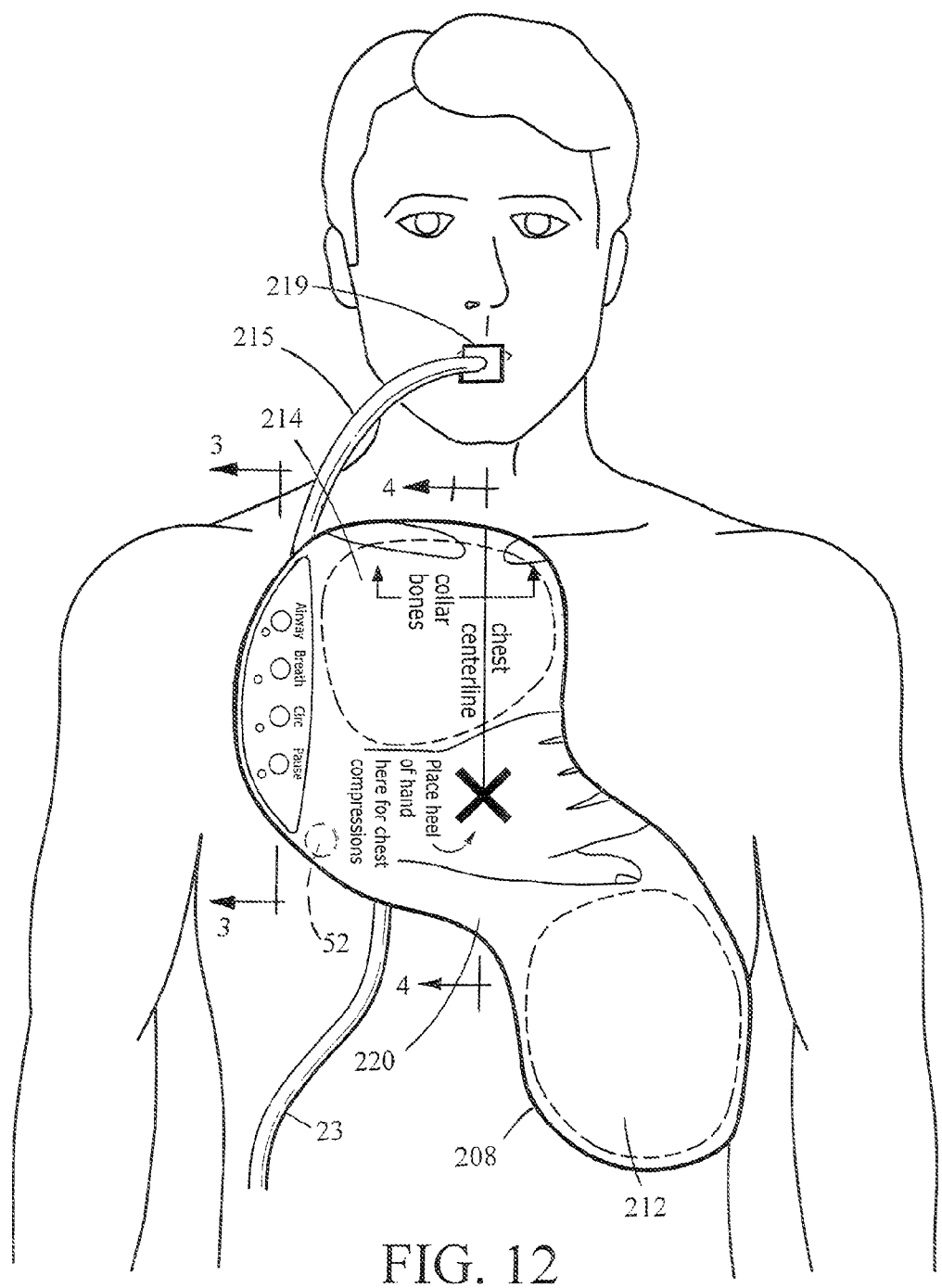
FIG. 12 shows an integrated electrode pad with integrated ventilation pressure sensor.
Figure 13:
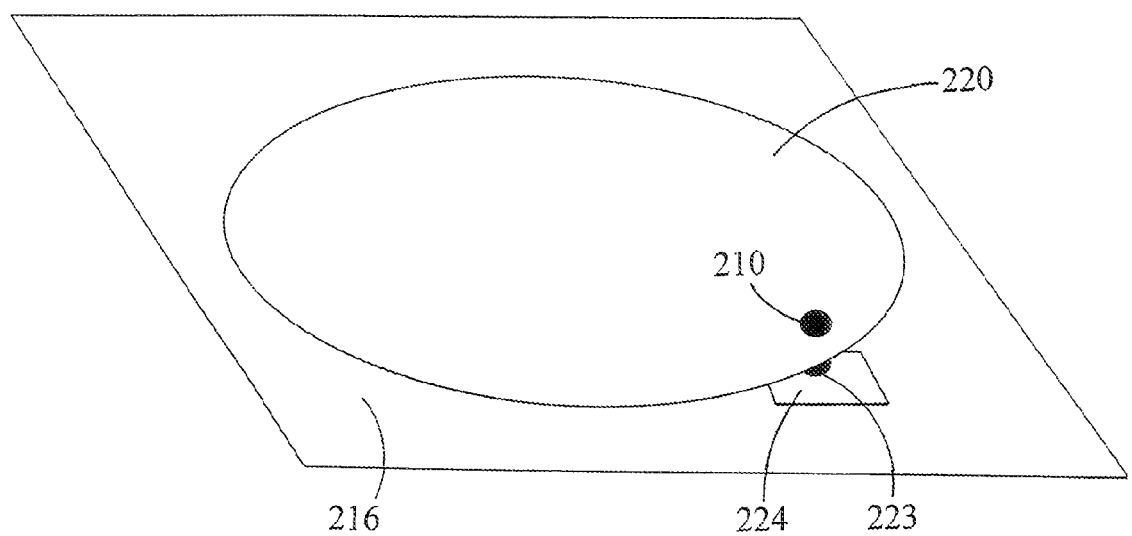
FIG. 13 is another view of an electrode pad.

Referring to FIGS. 12 and 13, in preferred implementations, a means is provided of detecting and differentiating successful completion of multiple steps of electrode application: (1) taking the electrodes 208 out of the storage area 222 or pouch 16; (2) peeling the left pad 212 from the liner 216; (3) peeling the right pad 214 from the liner 216; (4) applying the left pad 212 to the patient 218; and (5) applying the right pad 214 to the patient 218. Referring to FIGS. 12 and 13, a package photosensor 210 is provided on the outer face of the electrode backing 220. Detection that the electrode 208 is sealed in the storage area is determined by the photosensor output being below a threshold. A photoemitter/photosensor (PEPS) 223 combination is embedded into each electrode facing towards the liners 216. The liner 216 is constructed so that a highly reflective aluminized Mylar, self-adhesive disk 224 is applied to the liner 216 in the location directly beneath the PEPS 223. The reflective disk 224 is coated with a silicone release material on the side in contact with the electrode 208 so that it remains in place when the electrode 208 is removed from the liner. In such a configuration, the processor is fully capable of differentiating substantially the exact step in the protocol related to electrode application. When the package photosensor 210 detects light above a certain threshold, it is known that the electrodes have been removed from the storage area 222 or pouch 16. The high reflectance area 224 beneath each PEPS 223 provides a signal that is both a high intensity as well as being synchronous with the emitter drive with low background level; thus it is possible to distinguish with a high degree of accuracy which, if either, of the electrodes 212, 214 is still applied to the liner 216. When an electrode 212, 214 is removed from the liner 216 the background level of the signal increases due to ambient light while the synchronous portion decreases because there is little if any of the photoemitter light reflected back into the photosensor; this condition describes when an electrode 212, 214 is removed from the liner 216. When it has been determined that an electrode 212, 214 has been removed from the liner 216, the processor means 20 proceeds to the next state—looking for application of that electrode to the patient. Application of the electrode 212, 214 to the patient will result in a decrease in the background level of the signal output and some synchronous output level intermediate to the synchronous level measured when the electrode 212, 214 was still on the liner 216. If it has been determined that both electrodes 212, 214 are applied to the patient 218 but there is an impedance measured between the electrodes that is significantly outside the normal physiological range then it is very possible that the user has applied the electrodes to the patient without removing the patient's shirt. Surprisingly, this is not uncommon in real situations with users; a patient's shirt will have been only partially removed when electrodes are applied resulting in insufficient electrical contact with the patient's skin. FIG. 6d shows the flowchart for prompting related to retrieval and application of electrodes. As in the case with responding to a user's interactions.

In other implementations, the graphics on the center decal can be accompanied by any desired light source. For instance, if desired, all of the graphics can be translucent, and can be backlit. Alternatively, the graphics can be provided in the form of LED images, rather than on a decal.

While the electrodes have been illustrated in the form of an integral electrode assembly, separate electrodes may be used.

In some implementations, generally all of the graphically illustrated steps are shown at the same time, e.g., as illustrated by the decal described above. This arrangement allows the caregiver to see the steps that will be performed next and thus anticipate the next step and begin it early if possible. However, alternatively, the graphics can be displayed one at a time, e.g., by using a screen that displays one graphic at a time or backlit graphics that are unreadable when not back lit. This arrangement may in some cases avoid overwhelming novice or lay rescuers, because it does not present the caregiver with too much information all at the same time.

If desired, each graphic could have an associated button that, when pressed, causes more detailed audio prompts related to that graphic to be output by the defibrillator.

Figure 11:
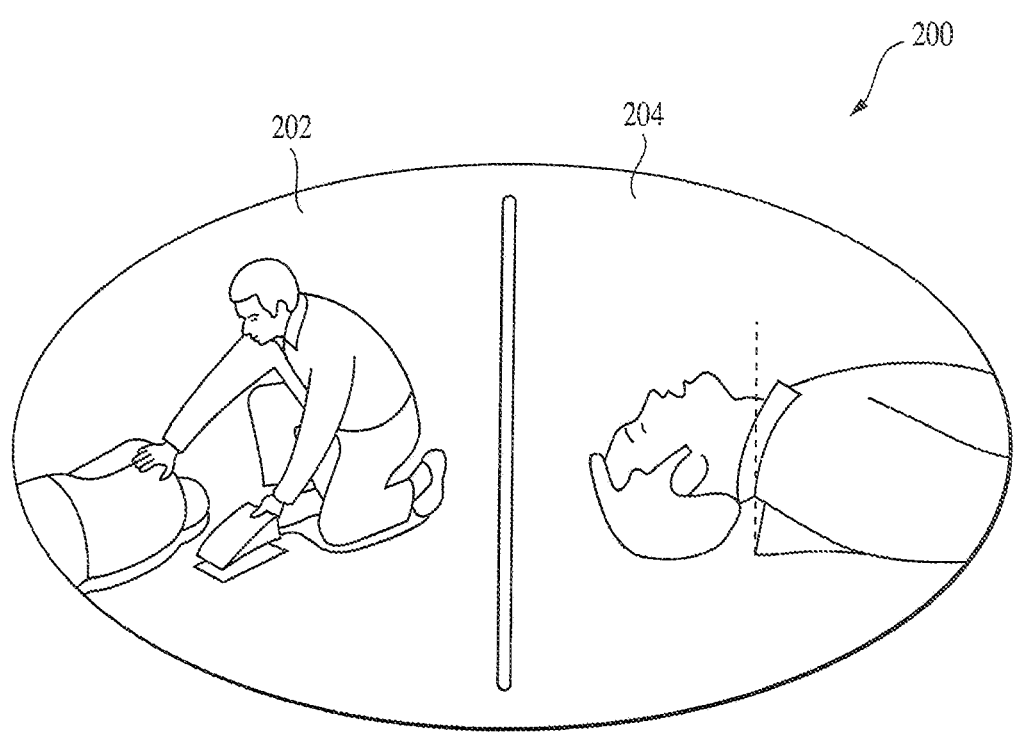
FIG. 11 is a plan view of a decal providing graphical instructions on the cover for placing the cover under a patient's shoulders.

The cover 12 of the AED may include a decal on its underside, e.g., decal 200 shown in FIG. 11. Decal 200 illustrates the use of the cover as a passive airway support device, to keep the patient's airway open during resuscitation. Graphic 202 prompts the caregiver to roll the patient over and place cover 12 under the patient's shoulders, and graphic 204 illustrates the proper positioning of the cover 12 under the patient to ensure an open airway.

Figure 5:
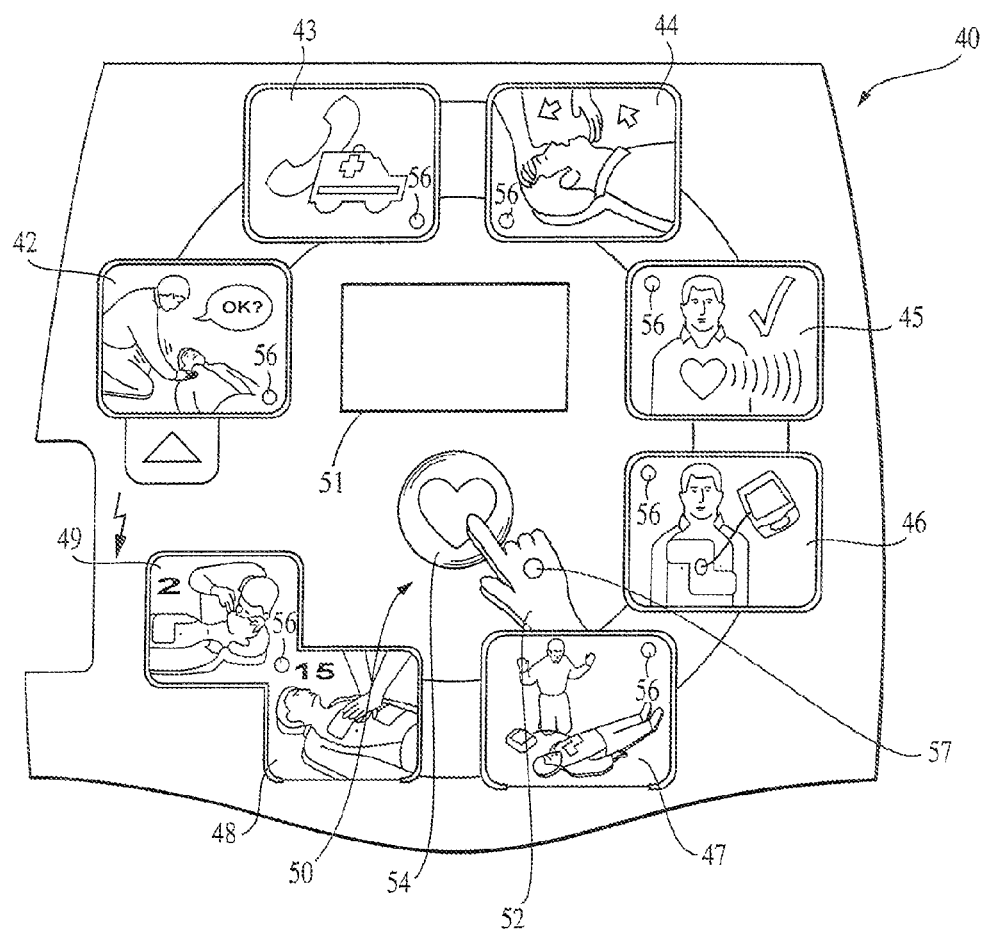
FIG. 5 is a plan view of the graphical interface decal used on the device housing of the AED of FIG. 1, as shown in FIG. 2.

While such a graphic is not included in the decal shown in FIG. 5, the decal 40 may include a graphic that would prompt the user to check to see if the patient is breathing. Such a graphic may include, e.g., a picture of the caregiver with his ear next to the patient's mouth. The graphic may also include lines indicating flow of air from the patient's mouth.

"Illuminated", "light up", and similar terms are used herein to refer to both a steady light and a light of varying intensity (e.g., blinking). A blinking light may be used, if desired, to more clearly draw the user's attention to the associated graphic.

Figure 16:
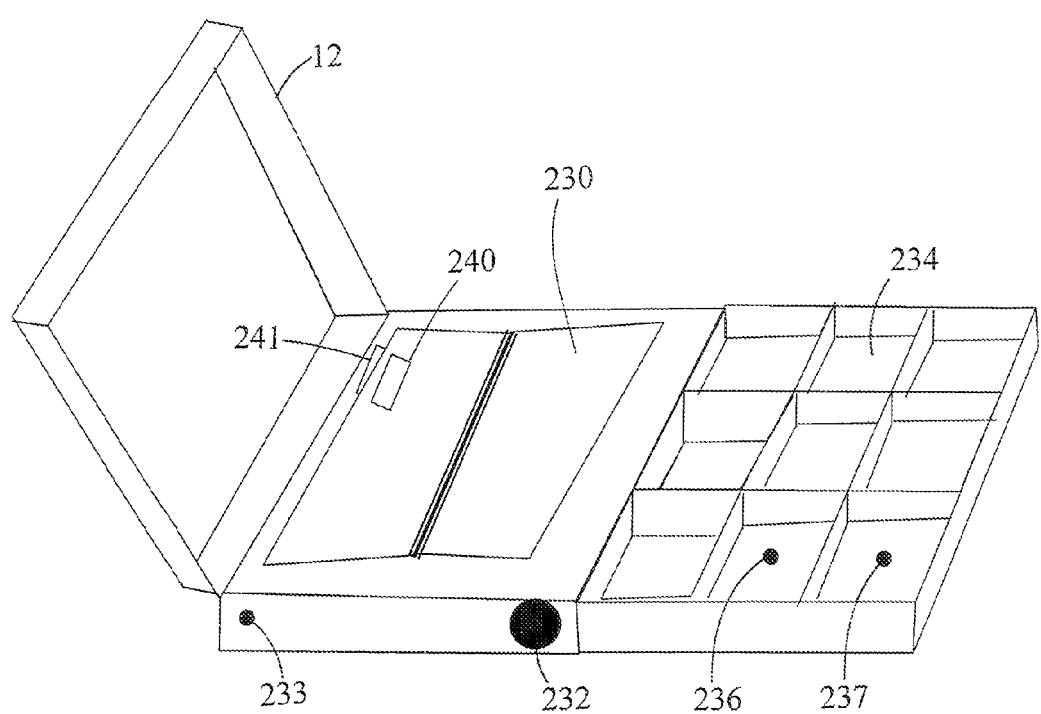
FIG. 16 is an isometric view of a first-aid kit implementation.

Referring to FIG. 16, in other implementations, a home first aid device may be provided for providing instructions and therapy, as needed, for a variety of medical situations. In some implementations, the device would include: (a) a cover to the device whose removal the processor is capable of detecting; (b) a series of bound pages 230 on the face of the device under the cover 12 with a detection means providing for determining to which page the bound pages have been turned; (c) a processor; (d) a speaker 232 providing audio output. The home first aid device may also include a portion of the device used specifically for storage of items commonly used in the course of providing aid such as bandaids, bandages, splints, antiseptic, etc. The storage area preferably takes the form of a partitioned tray 234. Alternatively, the storage area may take the form of multiple pockets, pouches, straps, or slots. The storage area is partitioned into individual wells in which each of the items is stored. Photoelectric sensors 236, 237 may be provided in each of the wells, thereby providing a means of determining which, if any, of the items has been removed by the user. Detecting which page the bound pages are turned to may be provided by embedding small high magnetic intensity samarium cobalt magnets 240 in locations specific to each page 242. In some implementations, the magnets 240 are located along the bound edge of the pages 242, outside the printed area of the pages 242. Magnetic sensors 241 are located in the device housing 14 that correspond to the locations where the magnets 240 located in the specific pages 242 make contact when the specific page 242 is turned. The magnetic sensor 241 may be a semiconductor device employing the Hall effect principle, but may also be a reed switch or other magnetically activated switch. By providing a means of detecting user actions automatically such as the detection of which page the user has turned to or which first aid item has been removed from the storage container, the device is able to interact and respond to the rescuer in an invisible manner, improving both speed as well as compliance to instructions. In such a manner, interactivity is preserved while at the same time providing a printed graphical interface to the user.

Figure 3A:
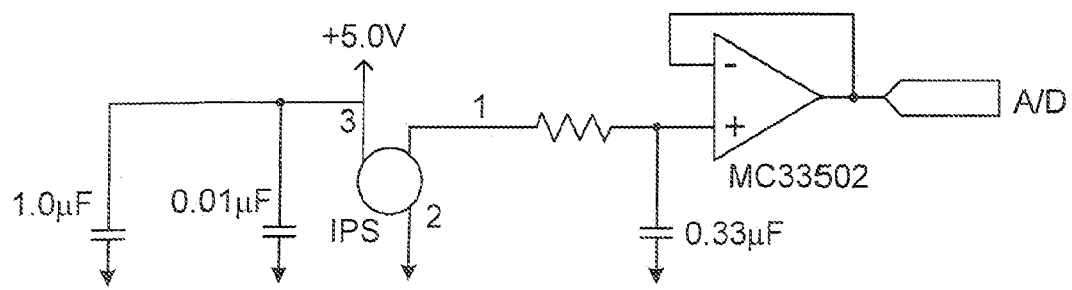
FIG. 3A is a circuit schematic showing filtering of the ventilation pressure sensor output.
Figure 4:
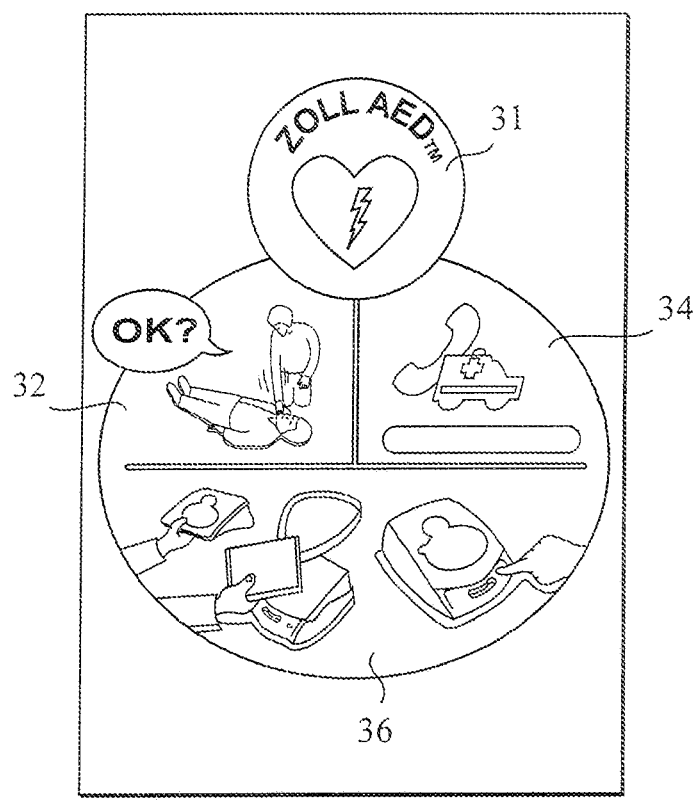
FIG. 4 is a plan view of the graphical interface decal used on the cover of the AED of FIG. 1.

In some implementations, a pressure sensor 21 (PS) may be provided (FIG. 3), e.g., the MPXV5004 pressure sensor manufactured by Freescale Semiconductor. The MPXV5004 has trimmed outputs, built-in temperature compensation, and an amplified single-ended output, which make it compatible with an Analog to Digital converter (A/D). The MPXV5004 uses a piezo-resistive pressure sensing element, which can produce shot (white) noise and 1/f (flicker noise). Shot noise is the result of non-uniform flow of carriers across a junction and is independent of temperature. Flicker noise (1/f) results from crystal defects, and is also due to wafer processing. This noise is proportional to the inverse of frequency and is more dominant at lower frequencies. Signal conditioning element 23 (FIG. 3) will filter out much of that noise. One possible circuit for accomplishing this filtering is shown in FIG. 3A.

Using the pressure sensor 21 configured as a gauge-type sensor, ventilation rates can be detected from variations in the generated pressure waveform. Conventional techniques may be used to process the pressure waveform to generate ventilation rate—e.g., template matching, bandpass filtering, or dynamic thresholding. The pressure sensor 21 may also be configured as a differential pressure sensor.

The pressure sensor may be located on the electrode pad assembly, as shown in FIG. 12. Tubing 215 is connected between the electrode assembly and an adapter 219 positioned in the airway. If a differential pressure measurement is being made, two tubes 215 are brought from the adapter to the electrode assembly. The adapter 219 has a small vane positioned between the pressure sensing ports so that the pressure difference generated between the two ports is proportional to the velocity of air flow through the adapter into the patient. Knowing the cross-sectional area of the air path through the adapter, allows the tidal volume to be estimated (using known differential pressure tidal volume measurement techniques).

Having calculated the ventilation rate and tidal volume, it is possible to detect whether or not the appropriate number and rate of breaths have been given as well as the proper amount of tidal volume. If the processor determines that the ventilation rate may be correct, but the tidal volume may be insufficient, a message may be generated, "Make sure to breathe more deeply into the patient" (prompt 13 in FIG. 7). Similar messages may also be provided to correct for incorrect ventilation rate.

In another implementation, an accelerometer 76 (FIG. 16) can be used instead of the pressure sensor. The accelerometer can be used to detect both the CPR compressions and the ventilation rate. Sternal displacement due to compressions has a high frequency leading edge and is initially negative (compression), while the ventilation cycle has a leading edge that is approximately an order of magnitude lower in frequency (0.5 Hz vs. 5 Hz) than the compression cycle, and is positive (chest rising due to lung inflation). Thus, ventilations can be distinguished from compressions, e.g., using a bandpass filter in the software detection algorithm. A limitation of this method is that accurate measurements of tidal volume would not normally be attainable.

In another implementation, the pressure sensor 21 can be combined with a second sensor, such as accelerometer 76, to detect the common clinical situation in which the intubation tube, commonly called the endotracheal (ET) tube, has been improperly positioned into the stomach via the esophagus, rather than into the lungs via the trachea. It is also not uncommon for the ET tube to become dislodged during the course of resuscitation, or as a result of vibrations during transport by ambulance or other mode of transportation. Detection of a pressure waveform pulse is used to initiate an analysis of either the accelerometer waveform, the TTI waveform, or both to see if the attempt to deliver respiratory gas via ventilation is delivering the gas to the lungs or to the stomach (via the esophagus). If the gas is delivered to the lungs, there will be an associated pulse waveform of the actual measured displacement of the sternal region where the accelerometer is placed (double integration of the accelerometer waveform will show a rising sternum). Alternatively, a TTI measurement can be used, as air delivered to the lungs will cause a rise in transthoracic impedance (TTI). Due to both the compressible nature of the gas as well as the fact that the lungs expand both sternally and diaphragmatically, there will be some delay following generation of the pressure pulse before the associated displacement waveform is observed from the accelerometer or the TTI measurement.

In some implementations, two pulse detection methods are used. The first time aligns the pressure waveform pulse with the pulse waveform of the sternal displacement and TTI measurement. If the delay from the leading edge of the pressure pulse waveform to the leading edge of the displacement and TTI waveforms is less than 700 milliseconds, and the delay of the trailing edge of the pressure pulse waveform to the trailing edge of the displacement and TTI waveforms is also less than 700 milliseconds, then the displacement and TTI pulse waveforms are considered to be as a result of the ventilation cycle. The second pulse detection method uses the acceleration waveform to detect the first initial movement of the sternum due to the ventilation. The displacement waveform is calculated, and the first pulse of the acceleration signal that contributes to the displacement pulse determines the start of the sternal displacement pulse. A more accurate onset of motion of the sternum due to ventilation can oftentimes be achieved in this manner.

If the displacement and TTI waveforms are found to be the result of the ventilation pressure waveform pulse, then the ET tube is considered to be in the proper location in the trachea and not in the esophagus.

A visual indicator comparable to those shown in FIG. 12 may be located on the electrode assembly, providing visual feedback to the rescuer as to whether or not the ET tube has been properly placed. When the tube is determined to be properly placed, the processing means mayl activate a green LED on the electrode assembly. If the previous ventilation attempt resulted in the determination of an improperly placed ET tube, then the processing means may activate a red LED of the visual indicator 216. The visual indicator may also include a series of LEDs configured as a dual color bar-graph to indicate the tidal volume of each successive ventilation, with the color of the LED bars indicative of whether or not the tube is properly placed (green indicating proper placement; red-indicating improper placement). Alternatively, separate indicating lights may be provided for airway and breathing, to indicate proper ET tube placement and ventilation tidal volume, respectively.

Many other implementations are within the scope of the following claims.

What is claimed is:

1. A device for assisting a caregiver in delivering cardiac resuscitation to a patient, the device comprising
    a user interface configured to deliver prompts to a caregiver to assist the caregiver in delivering cardiac resuscitation to a patient;
    a motion sensor positioned and configured to detect a movement of the chest wall of the patient;
    a processor configured to determine an estimate of the delivered ventilation rate from an output of the motion sensor and to distinguish between ventilations and chest compressions based at least in part on the shape of the leading edge of detected movement for determining the estimate; and
    a memory in which a plurality of different prompts are stored, including at least one ventilation progress prompt pertaining to the estimate of the delivered ventilation rate,
    wherein the processor is further configured to select a ventilation progress prompt based at least in part on the estimate of the delivered ventilation rate.

2. The device of claim 1 wherein the processor determines the estimate of the ventilation rate without using information from an airway pressure sensor.

3. The device of claim 1 wherein the processor determines the estimate of the ventilation rate using information from both the motion sensor and an airway pressure sensor.

4. The device of claim 1 wherein the processor is further configured to estimate a chest compression rate from the output of the motion sensor.

5. The device of claim 1 wherein the processor is configured to examine a sharpness of the leading edge, wherein greater sharpness is suggesting a chest compression.

6. The device of claim 5 wherein the processor is further configured to examine a frequency content in the leading edge, with higher frequency content suggesting the chest movements result from chest compressions.

7. The device of claim 5 wherein the processor is configured so that generally the sharper the leading edge and the higher the frequency content the more likely that the processor determines that the waveform detected by the motion sensor is a chest compression and not a ventilation.

8. The device of claim 1 wherein the processor is further configured to consider a direction of the movement of the chest wall at the leading edge, with downward displacement increasing the likelihood that the movement is a chest compression.

9. The device of claim 1 wherein the processor is configured to apply a bandpass filter to the output of the motion sensor as part of making the determination of whether the movement is a ventilation or a chest compression.

10. The device of claim 1 wherein the motion sensor comprises an accelerometer.

* * * * *